(12) United States Patent
Henstra et al.

(10) Patent No.: US 11,460,419 B2
(45) Date of Patent: Oct. 4, 2022

(54) ELECTRON DIFFRACTION HOLOGRAPHY

(71) Applicant: FEI Company, Hillsboro, OR (US)

(72) Inventors: Alexander Henstra, Eindhoven (NL); Yuchen Deng, Eindhoven (NL); Holger Kohr, Eindhoven (NL)

(73) Assignee: FEI Company, Hillsboro, OR (US)

( * ) Notice: Subject to any disclaimer, the term of this patent is extended or adjusted under 35 U.S.C. 154(b) by 362 days.

(21) Appl. No.: 16/835,129

(22) Filed: Mar. 30, 2020

(65) Prior Publication Data

US 2021/0302333 A1 Sep. 30, 2021

(51) Int. Cl.
*G01N 23/20* (2018.01)
*G01N 33/38* (2006.01)
*G03H 5/00* (2006.01)
*H01J 37/04* (2006.01)
*H01J 37/26* (2006.01)
*G01N 23/207* (2018.01)

(52) U.S. Cl.
CPC ......... *G01N 23/207* (2013.01); *G01N 33/385* (2013.01); *G03H 5/00* (2013.01); *H01J 37/04* (2013.01); *H01J 37/26* (2013.01); *G01N 2223/0566* (2013.01); *G01N 2223/064* (2013.01); *G03H 2224/04* (2013.01); *H01J 2237/2614* (2013.01)

(58) Field of Classification Search
CPC .............. G01N 23/207; G01N 33/385; G01N 2223/0566; G01N 2223/064; G03H 5/00; G03H 2224/04; H01J 37/04; H01J 37/26; H01J 2237/2614

USPC .......... 250/306, 307, 309, 310, 311
See application file for complete search history.

(56) References Cited

U.S. PATENT DOCUMENTS

| 11,183,364 | B1 * | 11/2021 | Deng | ................ H01J 37/28 |
|---|---|---|---|---|
| 2008/0094710 | A1 | 4/2008 | Endoh | |
| 2008/0149833 | A1 | 6/2008 | Endoh et al. | |
| 2019/0242819 | A1 * | 8/2019 | Frumker | ............. H01S 3/005 |
| 2021/0215472 | A1 * | 7/2021 | He | ............. G01B 9/04 |

OTHER PUBLICATIONS

EP21164757.3, Extended European Search Report, dated Aug. 31, 2021, 6 pages.
Tanji T., et al., "Differential Microscopy by Conventional Electron Off-Axis Holography", Applied Physics Letters, AIP Publishing LLC, US, vol. 69, No. 18, Oct. 28, 1996 (Oct. 28, 1996), pp. 2623-2625, XP012016405, DOI: 10.1063/1.117555.

* cited by examiner

*Primary Examiner* — Nicole M Ippolito

(57) ABSTRACT

Methods for using electron diffraction holography to investigate a sample, according to the present disclosure include the initial steps of emitting a plurality of electrons toward the sample, forming the plurality of electrons into a first electron beam and a second electron beam, and modifying the focal properties of at least one of the two beams such that the two beams have different focal planes. Once the two beams have different focal planes, the methods include focusing the first electron beam such that it has a focal plane at or near the sample, and focusing the second electron beam so that it is incident on the sample, and has a focal plane in the diffraction plane. An interference pattern of the first electron beam and the diffracted second electron beam is then detected in the diffraction plane, and then used to generate a diffraction holograph.

20 Claims, 16 Drawing Sheets

ELECTRON DIFFRACTION HOLOGRAPHY

CROSS REFERENCE TO RELATED APPLICATIONS

This application relates to patent application Ser. No. 16/834,963, filed on Mar. 30, 2020, titled "Dual Beam Bifocal Charged Particle Microscope", by Henstra et al., which is incorporated herein by reference in its entirety and for all purposes.

BACKGROUND OF THE INVENTION

A transmission electron microscope can be operated in Selected Area Electron Diffraction (SAED) mode, in which the diffraction plane is imaged onto a camera. This mode is especially useful for the study of crystalline material, in which case crystallographic information can be obtained. In the case where a single (monocrystalline) crystal is studied, diffraction patterns can even be used for the reconstruction of the 3D potential distribution of the atoms that constitute the crystal. For isotropic resolution, diffraction patterns need to be collected for all orientations of the crystal. In practice, data is usually collected while continuous tilting of the crystal over an appropriate range. This technique is called micro Electron Diffraction, or 3D electron crystallography. Diffraction peak intensities only provide structure factor amplitudes, phase information is missing and has to be obtained by other methods. If the diffraction peaks extend to high resolution (order 1 Angstrom) and the number of atoms in the unit cell is limited, phases can be derived computationally using certain constraints (atomicity, phase correlations). For larger molecules and lower resolution, a method called 'molecular replacement' is often used, using phase information from homologue structures as initial guess for the phase. For entirely unknown structures this cannot be done. Other popular phasing methods as used in X-ray crystallography (anomalous dispersion, isomorphous replacement) are not well applicable for electron crystallography.

Moreover, current transition electron microscopy (TEM) systems operating in electron diffraction mode struggle to obtain the full exit wave (of the specimen i.e., the complex exit wave including both amplitude and phase information). Instead, TEM systems operating in electron diffraction mode merely record the intensity of scattered and/or diffracted electrons at various points in a detector positioned in a magnified image of the diffraction plane, and then generate a reconstruction of the specimen based only on the detected intensity values (i.e., without phase information). This inability to determine phase information limits the types of objects that can be effectively imaged by TEM systems operating in electron diffraction mode. While current electron holography setups exist that allow for both intensity and phase information to be obtained via superposition of a coherent wave with the electrons scattered and/or diffracted electrons by an object, these systems are unable to generate results from electrons scattered and/or diffracted electrons that are detected in the diffraction plane. For example, off-axis holography is a well-known technique that has been developed to obtain full exit waves of a specimen, but currently this technique can only be only applied where the specimen is imaged onto the camera.

SUMMARY OF THE INVENTION

Methods for using electron diffraction holography to investigate a sample, according to the present disclosure include the initial steps of emitting a plurality of electrons toward the sample, forming the plurality of electrons into a first electron beam and a second electron beam, and then modifying the focal properties of at least one of the first electron beam and the second electron beam such that the two electron beams have different focal planes. Once the two beams have different focal planes, methods according to the present invention include the additional steps of focusing the first electron beam such that it has a focal plane at or near the sample, and focusing the second electron beam so that it is incident on the sample, and has a focal plane in the diffraction plane. An interference pattern of the first electron beam and the diffracted second electron beam is then detected in the diffraction plane, and then used to generate a diffraction holograph.

Systems for investigating a sample using electron holography, according to the present disclosure comprise a sample holder configured to hold a sample, an electron emitter configured to emit electrons towards the sample, and a bifocal beamformer positioned between the electron emitter and the sample holder. The bifocal beamformer is configured to form the plurality of electrons into a first electron beam and a second electron beam, and modify the focal properties of at least one of the first electron beam and the electron particle beam. The modified focal properties of the first electron beam and the second electron enables another component of the system (e.g., a stigmator) to cause the corresponding focal planes of the first electron beam and the second electron beam to be different. In some embodiments, the bifocal beamformer modifies the focal properties of at least one of the beams such that the first electron beam is focused at a plane at or near the sample and the second electron beam is not focused at the plane at or near the sample.

BRIEF DESCRIPTION OF THE DRAWINGS

The detailed description is described with reference to the accompanying figures. In the figures, the left-most digit(s) of a reference number identify the figure in which the reference number first appears. The same reference numbers in different figures indicates similar or identical items.

Figure 1:
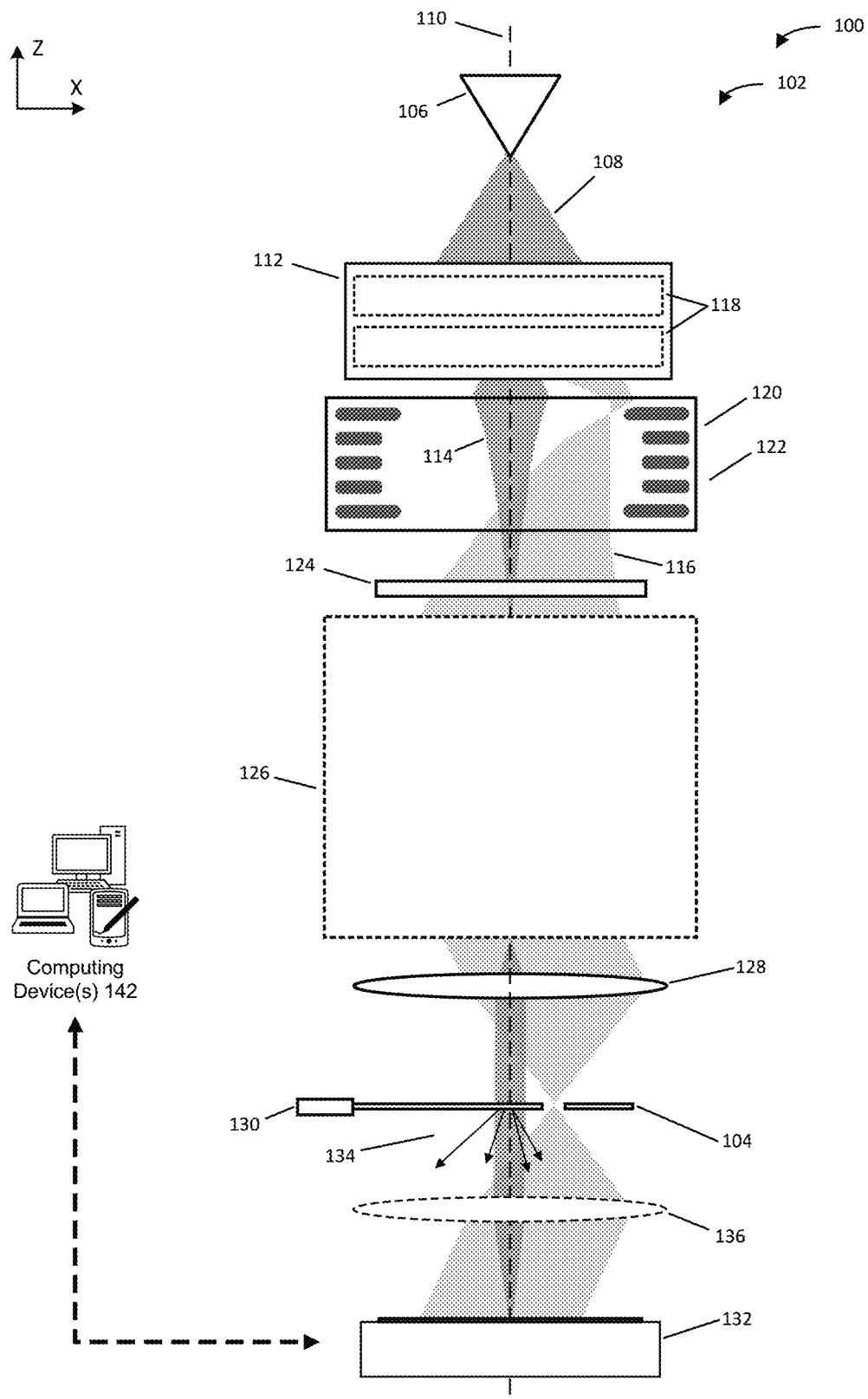
FIG. 1 illustrates example bifocal multibeam systems for using diffraction holography to investigate a sample according to the present invention.

Like reference numerals refer to corresponding parts throughout the several views of the drawings. Generally, in the figures, elements that are likely to be included in a given example are illustrated in solid lines, while elements that are optional to a given example are illustrated in broken lines. However, elements that are illustrated in solid lines are not essential to all examples of the present disclosure, and an element shown in solid lines may be omitted from a particular example without departing from the scope of the present disclosure.

DETAILED DESCRIPTION OF EMBODIMENTS

Methods and systems for performing electron diffraction holography, are included herein. More specifically, the methods and systems disclosed herein include and/or are configured to allow for diffraction holograms of a sample to be generated from interference patterns between an in-focus electron beam and a wide reference electron beam that are detected in the diffraction plane. In the methods and systems, a plurality of electrons that have been emitted by an electron source are split into a coherent first and second electron beam, and the focal properties of at least one of the first electron beam and the second electron beam are modified such that corresponding focal planes of the first electron beam and the second electron beam are different. In some embodiments, the focal plane of at least one of the first electron beam and the second electron beam is modified such that the first electron beam is focused at a plane at or near the sample, and the second electron beam is made to be a parallel (or almost parallel), convergent, or divergent beam when incident on the sample. In various embodiments, the first electron beam passes through an aperture in the sample and/or a thin portion of the sample such that it is not substantially affected by the sample, allowing the first electron beam to serve as a reference beam. An interference pattern of the first electron beam and the diffracted second electron beam is then detected in the diffraction plane, and then used to generate a diffraction hologram. The diffraction hologram provides both phase and amplitude of the diffraction pattern.

For example, when the above process is used in microelectron diffraction, diffraction holograms of a sample (e.g., a crystal) may be obtained at a plurality of sample tilts to determine information for the sample (e.g., phase and amplitude of diffraction peaks). Alternatively, the above processes may be used to generate a single diffraction hologram of a sample (e.g., crystalline, multi-crystalline, partly crystalline, non-crystalline, etc.) from which holographic techniques can be used to determine the full exit wave of the specimen (i.e., a complex exit wave including both phase and amplitude) can be retrieved. If this is repeated to obtain the full exit wave of the specimen at multiple sample tilts then 3D information (i.e., tomography) can be obtained using the above process. In some embodiments, the plurality of electrons are split and/or modified at least partially by a bifocal beamformer. The bifocal beamformers according to some embodiments of the present invention are configured to apply a at least a quadrupole lensing effect to at least one of the first electron beam and the second electron beam. In some embodiments, the bifocal beamformers causes the focal planes of the two electron beams to be different. Alternatively, in some embodiments, the bifocal beamforms causes a change in the focal properties of at least one of the electron beams such that, when the beams are passed through a multipole element (i.e., a multipole/corrector/stigmator that applies at least a quadrupole lensing effect) downstream of the bifocal beamformer, the corresponding focal planes of the two beams are caused to be different. For example, one beam may be caused to have a focal plan at a sample, and the other beam may have a corresponding focal plane at least 0.1%, 1%, 10%, or 100% of the objective lens focal distance above and/or below the specimen. The diameter of one beam at the sample may be at least one of 50, 100, 500, or 1000 times greater than the diameter of the other electron beam (i.e., the geometric spot size). Alternatively, or in addition, the diameter of one beam at the sample may be at least one of 50, 100, 500, or 1000 times greater than the diameter of the other electron beam when the other electron beam is in focus.

FIG. 1 is an illustration of bifocal multibeam system(s) 100 that is set up to conduct diffraction holography, according to the present invention. Specifically, FIG. 1 illustrates an example bifocal multibeam system(s) 102 for using diffraction holography to investigate a sample 104. The example bifocal multibeam system(s) 102 may include electron microscope (EM) setups or electron lithography setups that are configured to irradiate and/or otherwise impinge the sample 104 with at least two beams of electrons that have different corresponding focal planes. In various embodiments, the bifocal multibeam system(s) 102 may be or include one or more different types of EM and/or charged particle microscopes, such as but not limited to, a scanning electron microscope (SEM), a scanning transmission electron microscope (STEM), a transmission electron microscope (TEM), a charged particle microscope (CPM), dual beam microscopy system, etc. Additionally, in some embodiments, a bifocal multibeam system(s) 102 may be a TEM which is capable of operating as a STEM as well.

The example bifocal multibeam system(s) 102 includes an electron source 106 (e.g., a thermal electron source, Schottky-emission source, field emission source, etc.) that emits a plurality of electrons 108 (i.e., an electron beam) along an emission axis 110 and towards a bifocal beamformer 112. The emission axis 110 is a central axis that runs along the length of the example bifocal multibeam system(s) 102 from the electron source 106 and through the sample 104.

The bifocal beamformer 112 is one or more structures configured to (i) split the plurality of electrons 108 into at least a first electron 114 and a beam second electron beam 116, and (ii) modify the focal properties of at least one of the first electron beam 114 and a second electron beam 116. For example, the bifocal beamformer 112 may modify the focal properties such that the first electron beam 114 and the second electron beam 116 have different corresponding focal planes. FIG. 1 illustrates the bifocal beamformer 112 as splitting the plurality of electrons 108 into a first electron beam 114 that runs along the emission axis 110 and a second electron beam 116. Because each of the first electron beam 114 and the second electron beam 116 are formed from the plurality of electrons 108, the first electron beam 114 and a second electron beam 116 are mutually coherent.

FIG. 1 also shows the bifocal beamformer 112 as applying a distortion to the second electron beam 116 that causes the focal properties of the second electron beam to differ from the focal properties of the first electron beam 114. For example, FIG. 1 illustrates the bifocal beamformer 112 as being configured to generate at least a quadrupole field (i.e. dipole field, quadrupole field, hexapole field, octupole field, etc.) that applies a quadrupole lensing effect that affects the second electron beam 116 such that the two beams have a different focal properties. The at least a quadrupole lensing effect may distort, stigmate, or otherwise modify at least one of the beams such that the corresponding focal properties of the beams are made different. In some embodiments, the quadrupole lensing effect may apply a different lensing effects in one meridional plane (e.g. an x-z plane) than in a perpendicular meridional plane (e.g., a y-z plane), causing a different change to each of the focal properties in each of the two meridional planes. Such a stigmation is illustrated in the example system shown in FIG. 4.

In such embodiments, a multipole element (e.g., a stigmator) downstream of the bifocal beamformer may apply a complimentary quadrupole lensing effect to the one of the second electron beam 116 to correct for aberrations caused by the bifocal beamformer 112, and cause the second electron beam 116 to become a cylindrically symmetric beam again. In this way, the multipole element causes the second electron beam 116 to be cylindrically symmetric cylindrically symmetric downstream of such a multipole element while also having different focal planes from the first electron beam 114. In various setups this multipole element may be placed in a focal plane of the first electron beam 114 so that the complementary quadrupole lensing effect is not applied to the first electron beam 114.

In some embodiments, the bifocal beamformer 112 is configured to modify the focal properties of at least one of the first electron beam 114 and the second electron beam 116 such that the second electron beam 116 has a focal plane at a specimen plane at or near the sample 104 and the first electron beam 114 has a corresponding focal plane that is not at the specimen plane at or near the sample 104. In various embodiments, the bifocal beamformer 112 may modify the focal plane of the first electron beam 114 such that it is focused at a plane which is located at least 0.1%, 1%, 10%, or 100% of the objective lens focal distance above or below the sample 104. Alternatively, the bifocal beamformer 112 may modify the focal properties of at least one of the electron beams such that the first electron beam 114 has a focal plane at a specimen plane at or near the sample 104 and the second electron beam 116 has a corresponding focal plane that is not at the specimen plane at or near the sample 104. In such embodiments, the focal planes(s) may be modified such that the second electron beam 116 is focused at a plane which is located at least 0.1%, 1%, 10%, or 100% of the objective lens focal distance above and/or below the sample 104.

While FIG. 1 illustrates an embodiment where one of the beams is focused in the specimen plane (i.e., have a focal plane at or near the specimen plane), a person having skill in the art will understand that bifocal multibeam systems 100 according to the present invention do not require that either of the electron beams be focused in the specimen plane. Moreover, while the bifocal beamformer 112 is shown as modifying the focal properties of the second electron beam 116, in other embodiments the bifocal beamformer 112 may cause the focal properties of the first electron beam 114, or both beams to be changed, such that the two beams have different corresponding focal planes. That is, a person having skill in the art would understand that the actions or effects described as being applied to one beam may be applied to the other beam in a different embodiment to enable the two beams to have different corresponding focal planes.

Alternatively or in addition, the bifocal beamformer 112 may be configured to modify the focal properties of at least one of the first electron beam 114 and the second electron beam 116 such that the diameter of the first electron beam 114 at a specimen plane at or near the sample 104 is at least one of 20, 50, 100, 500, or 1000 times greater than the diameter of the second electron beam 116 at the specimen plane. In such embodiments, the bifocal beamformer 112 may cause the diameter of the first electron beam 114 to be at least one of 20, 50, 100, 500, or 1000 times greater than the diameter for the second electron beam 116 at any plane where the second electron beam 116 is in focus. In some embodiments, the bifocal beamformer 112 further causes one or both of the first electron beam 114 and the second electron beam 116 to be deflected away from the emission axis 110.

In some embodiments, the bifocal beamformer 112 may be composed of a single component that performs both the forming of the first electron beam 114 and the second electron beam 116 and the modification of the focal properties of at least one of the two beams. For example, the bifocal beamformer 112 may correspond to a microelectromechanical system (MEMS) that both forms the two beams and generates at least a quadrupole electromagnetic field (i.e. dipole field, quadrupole field, hexapole field, octupole field, etc.) which applies at least a quadrupole lensing effect that focuses, stigmates, and/or otherwise modifies at least one of the beams such that the corresponding focal properties of the beams are made different. In another example, the bifocal beamformer 112 may correspond to an aperture array comprising a structure defining a plurality of apertures and/or cavities that both form the two beams and create at least a quadrupole electromagnetic fields that applies the quadrupole lensing effect to one or more of the two beams. In some embodiments, the quadrupole lensing effect may apply a positive lensing in one meridional plane (e.g. an x-z plane) and a negative lensing effect in a perpendicular meridional plane (e.g., a y-z plane), causing a different change to each of the focal properties in each of the two meridional planes.

In such systems, a multipole element 124 (e.g., a corrector, a stigmator or a multipole element which is part of an aberration corrector, a corrector of the quadrupole/octupole type, etc.) may be included in the example bifocal multibeam system(s) 100 further downstream to apply a complementary quadrupole lensing effect to make the beam cylindrically symmetric again. For example, FIG. 1 illustrates the bifocal multibeam system(s) 102 as including a stigmator. Alternatively or in addition, the bifocal beamformer 112 may be positioned and/or configured to cause at least one of the one or more aberrations of the electron beams to correct another aberration in the bifocal multibeam system(s) 102. Such a system component may be positioned in a focal plane of the electron beam to which bifocal beamformer 112 did not apply at least a quadrupole lensing effect. In embodiments where the bifocal beamformer applies at least a first quadrupole lensing effect to the first electron beam 114 and a second quadrupole lensing effect to the second electron beam 116, such a bifocal multibeam system(s) 100 may include a first multipole element 124 positioned in a focal plane of the first electron beam 114 and configured to apply a complementary quadrupole lensing effect to the second electron beam 116, and a second multipole element 124 positioned in a focal plane of the second electron beam 116 and configured to apply a complementary quadrupole lensing effect to the first electron beam 114.

Alternatively, the bifocal beamformer 112 may be composed of a plurality of components 118. Individual components 118 may perform one of the forming of the first electron beam 114 and the second electron beam 116 and the modification of the focal properties of at least one of the two beams, or they may contribute to one or both of the forming the beams and modifying of focal properties in concert with other components 118. In some embodiments, the individual components 118 may include a physical structure that blocks a portion of the plurality of electrons 108 while allowing others to pass through, a biprism (e.g., a charged wire), an amplitude-division electron beam splitter made of thin crystals or nanofabricated gratings, a beam splitting laser system configured to use one or more lasers pattern fringes to split the plurality of electrons 108 into the first electron beam 114 and the second electron beam 116, etc. Alternatively, or in addition, the individual components 118 may include one or more lenses (e.g., an einzel lens, a quadrupole lens, etc.) that are positioned or otherwise configured to cause the first electron beam 114 and the second electron beam 116 to have different focal planes. For example, the bifocal beamformer 112 may be composed of a physical structure defining two apertures, and a lens positioned and/or configured to adjust the focal properties of the at least one of the first electron beam and the second electron beam such that they have different corresponding focal planes. In various embodiments, such a lens may be positioned above or below the physical structure.

FIG. 1 illustrates the bifocal beamformer 112 as being positioned upstream of focusing component 120 that is configured to apply a lensing action that focuses at least one of the first electron beam 114 and the second electron beam 116. Moreover, the focusing component 120 is positioned upstream of the multipole element 124. In the example bifocal multibeam system(s) 102 shown in FIG. 1, the focusing component corresponds to an accelerator 122 that accelerates/decelerates, focuses, and/or directs the first electron beam 114 and the second electron beam 116 towards a focusing column 126. However, in other embodiments, the accelerator 122 may be positioned between electron source 106 and the bifocal beamformer 112 such that the accelerator 122 accelerates/decelerates, focuses, and/or directs the electrons 108 to the bifocal beamformer 112, and the bifocal beamformer 112 splits and modifies the focal properties of electrons 108 at a final energy (e.g., 30 kV). In such embodiments, the focusing component 120 may correspond to a lens or other structure configured to apply a lens action that focuses at least one of the first electron beam 114 and the second electron beam 116.

The focusing column 126 focuses the electron beams 114 and 116 so that they are incident on sample 104. Specifically, FIG. 1 illustrates the focusing column 126 focusing the second electron beam 116 so that is focused on the sample 104 and the first electron beam 114 such that it is not focused on the sample 104. In some embodiments, one of the first electron beam 114 or second electron beam 116 may be parallel, substantially parallel, convergent, or divergent when it is incident on the sample 104. Moreover, in other embodiments, the focusing column 126 may cause the first electron beam 114 to be focused on the sample 104 and the second electron beam 116 to not be focused on the sample 104. In other embodiments the focusing column 126 may cause neither beam to be focused at the sample. While not illustrated in FIG. 1, those having skill in the art will understand focusing column 126 may include one or more correctors (e.g., a Cs or Cs+Cc aberration corrector), transfer lenses, deflectors, scan coils, beam blankers, etc. necessary to enable and/or enhance the investigation of the sample 104 with the bifocal multibeam system(s) 102.

FIG. 1 also shows the bifocal multibeam system(s) 102 as including an objective lens 128. The objective lens 128 is an optical element that focuses one of the first electron beam 114 and the second electron beam 116 to a point on the sample 104. The objective lens 128 may comprise a single-polepiece lens, a magnetic electrostatic compound lens, electrostatic detector objective lens, or another type of objective lens. For example, the objective lens 128 may correspond to a TEM objective lens in which the sample is immersed within the TEM objective lens and/or between the pre-specimen and post specimen components of the TEM objective lens. FIG. 1 further illustrates the bifocal multibeam system(s) 102 as including a sample holder 130 that holds the sample 104. FIG. 1 shows the first electron beam 114 as being a TEM beam that is incident on the sample 104 and the second electron beam 116 as being a reference beam that passes through an aperture in the sample 104 and/or a thin portion of the sample such that it is not substantially affected by the sample, allowing the second electron beam 116 to serve as a reference beam during electron diffraction holography.

FIG. 1 further shows the bifocal multibeam system(s) 102 as including a detector 132 positioned in the diffraction plane that is configured to detect the second electron beam 116 and the diffracted electrons 134 that pass through the sample 104 as a result of the electron beams 114 being incident on the sample 104. During electron diffraction holography, the detector 132 is configured to generate an interference pattern of the second electron beam and the diffracted first electron beam in the diffraction plane, and then used to generate a diffraction hologram and/or a hologram image of the sample. Such an embodiment may further include one or more projection lenses 136 positioned between the sample 104 and the detector 132. In some embodiments, zero-loss filtering may be applied during the generation of the diffraction hologram.

FIG. 1 further shows bifocal multibeam system(s) 102 as optionally including computing device(s) 142. In various embodiments, the computing device(s) 142 may be configured to determine, based on a known phase of the second electron beam 116 and the interference pattern detected by the detector 132, a diffraction hologram of the sample 104. Because the first electron beam 114 and the second electron beam 116 are mutually coherent, the computing devices 142 are able to determine the phase of the electrons diffracted by the sample. This further allows the computing devices 142 to determine both the phase and the amplitude of the diffraction pattern. For example, in micro-electron diffraction, the computing systems may obtain diffraction holograms of a crystal at multiple orientations of the crystal (i.e., sample tilts) to determine the phase and amplitude of the diffraction peaks. Such phase and amplitude information can be used to determine the structure and/or other crystallographic information about the crystal, even where no prior information was known about the crystal. Moreover, in some embodiments, the computing devices 142 are further configured to use the diffraction hologram to retrieve the specimen exit wave function (e.g., both amplitude and phase), and/or use the specimen exit wave function to determine the crystal lattice and/or a hologram image of the sample 104.

Those skilled in the art will appreciate that the computing devices 142 depicted in FIG. 1 are merely illustrative and are not intended to limit the scope of the present disclosure. The computing system and devices may include any combination of hardware or software that can perform the indicated functions, including computers, network devices, internet appliances, PDAs, wireless phones, controllers, oscilloscopes, amplifiers, etc. The computing devices 142 may also be connected to other devices that are not illustrated, or instead may operate as a stand-alone system.

Figure 2A:
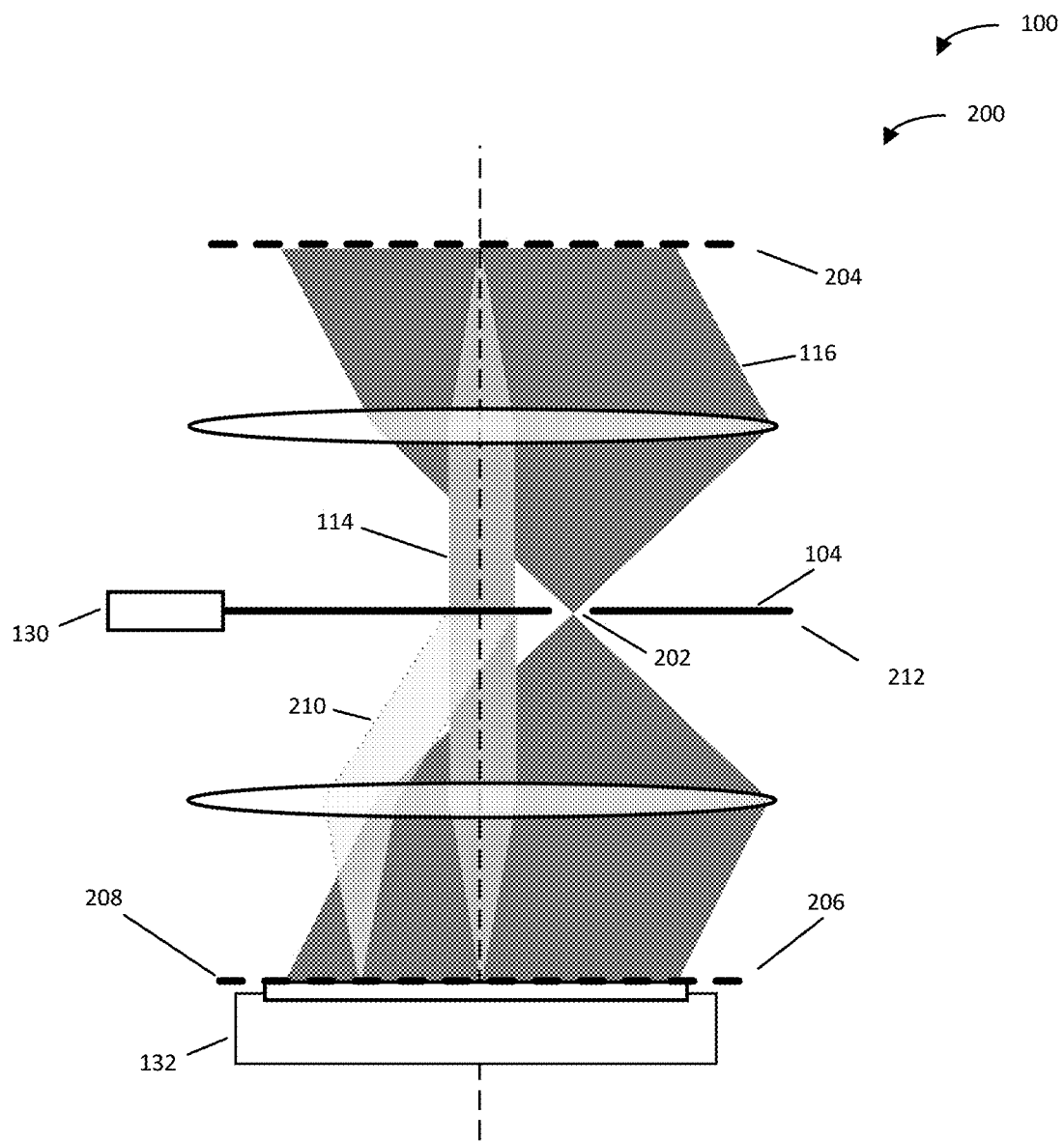
FIGS. 2A and 2B illustrate a first electron beam and a second electron beam interacting with the sample during electron diffraction holography in an example bifocal multibeam system.
Figure 2B:
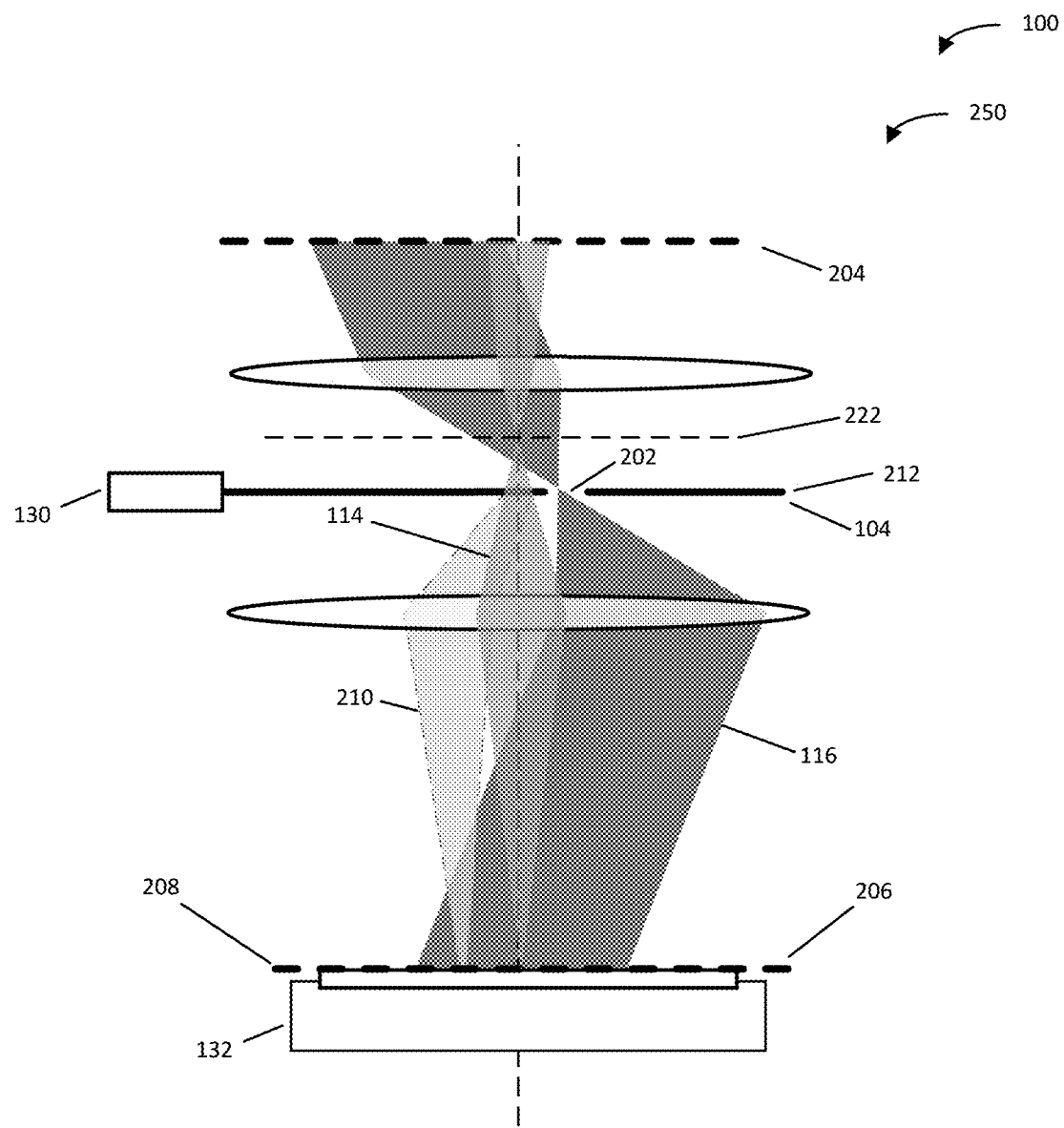

FIGS. 2A and 2B are illustrations of the first electron beam and the second electron beam interacting with the sample during electron diffraction holography in an example bifocal multibeam system 100.

Specifically, FIG. 2A illustrates the first electron beam 114 as being a TEM illumination beam that is substantially perpendicular to the sample plane at the sample 104, and the second electron beam 116 is shown as being a reference beam. However, in other embodiments the second electron beam 116 may act as the TEM illumination beam, and the first electron beam 116 may act as a reference beam. FIG. 2A shows the reference beam as passing through an aperture 202 in the sample 104. The aperture 202 may have any shape, such as circular, polynomial, ovoid, slit, etc. In other embodiments, the reference beam may pass through a thin portion of the sample such that it is not substantially affected by the sample. Alternatively, the reference beam may be directed so that it passes by the sample without passing through it. FIG. 2A shows the first electron beam 114 as being an axial beam, however in other embodiments the first electron beam 114 as being a non-axial beam. Similarly, while FIG. 2A illustrates the second electron beam 116 as being a non-axial beam, in other embodiments the second electron beam 116 may be an axial beam.

FIG. 2A further shows the first electron beam 114 as having a front focal plane 204 positioned above the objective lens 130, and a back focal plane 206 that corresponds to the diffraction plane 208. FIG. 2A also illustrates a portion 210 of the first electron beam 114 that is scattered/diffracted by the sample 104. The detector 132 is positioned so as to detect both the portion 210 of the first electron beam 114 that is scattered/diffracted by the sample 104 and the second electron beam 116 in the diffraction plane 208. As understood by those in the art, the portion 210 and the second electron beam 116 form an interference pattern based on the structure and/or characteristics of the sample. For example, where the sample is a crystal, the interference pattern may correspond to a plurality of peaks (i.e., Airy disks).

Similarly, FIG. 2B illustrates an embodiment 250 of the present invention where the TEM illumination beam (shown in FIG. 2B as the electron beam 116) is a non-parallel beam at the specimen. Specifically, FIG. 2B shows a virtual diffraction plane 222 above the sample plane 212. While FIG. 2B shows the TEM illumination beam as being a divergent beam at the sample, in other embodiments the TEM illumination beam may be a convergent beam.

In the diffraction plane 208, the wave function of the diffracted portion 210 of the first electron beam 114 is the Fourier transform of the sample exit wave function. In this way, a pixel in the interference pattern detected in the diffraction plane 208 (i.e., diffraction hologram) corresponds to a spatial frequency in the sample exit wave. Because the two electron beams are mutually coherent, the complex exit wave in the sample plane 212 can be mathematically extracted from the interference pattern detected in the diffraction plane 208.

Figure 3:
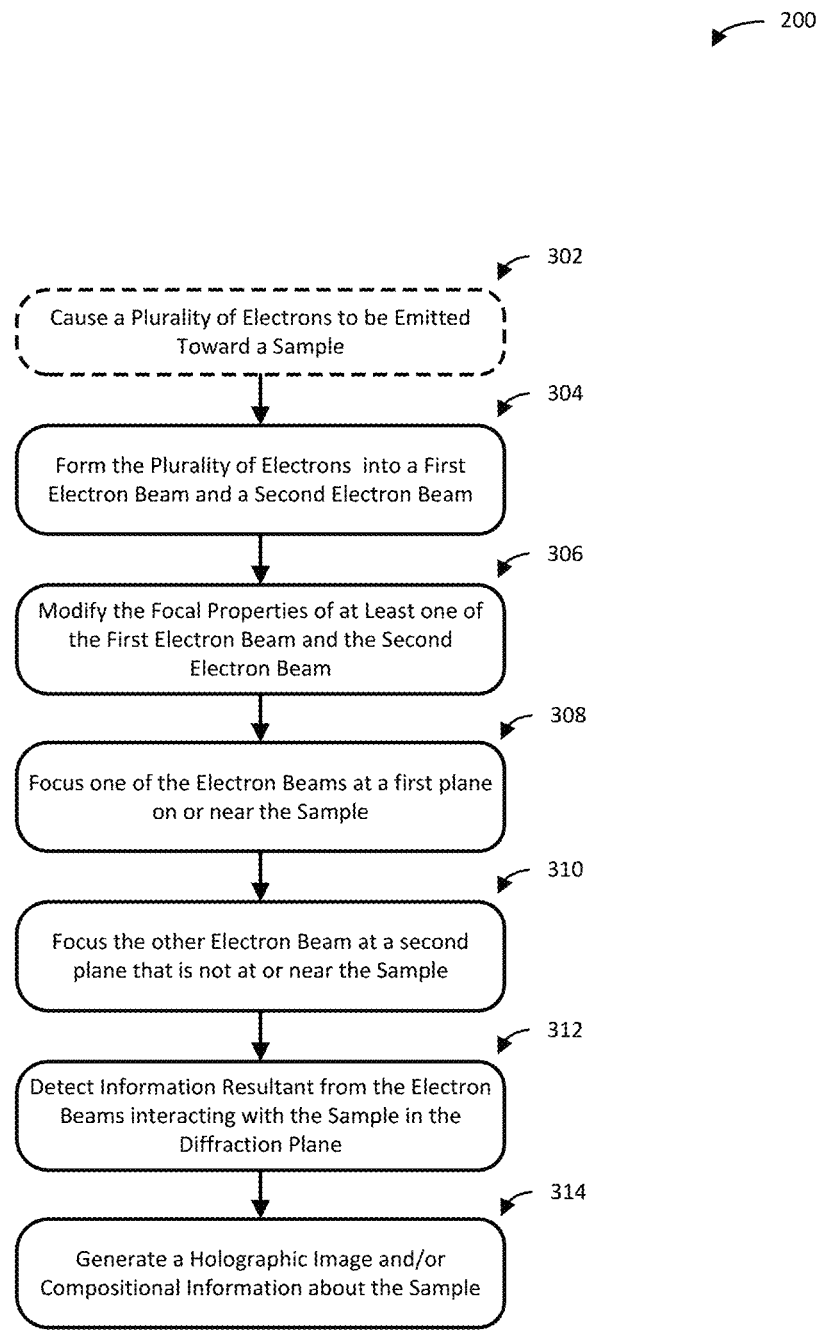
FIG. 3 illustrates a sample process for investigating a sample with diffraction electron holography using bifocal multibeam system according to the present invention.

FIG. 3 is a flow diagram of illustrative processes illustrated as a collection of blocks in a logical flow graph, which represent a sequence of operations that can be implemented in hardware, software, human operation, or a combination thereof. In the context of software, the blocks represent computer-executable instructions stored on one or more computer-readable storage media that, when executed by one or more processors, cause the performance of the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the processes.

FIG. 3 is a depiction of a sample process 300 for investigation of a sample with diffraction electron holography using bifocal multibeam system(s) 100 according to the present invention. The process 300 may be implemented in any of the example microscope system(s) 100, 700, 1200, and 2400.

At 302, a plurality of electrons are emitted towards a sample by an electron source. The electron source may include a thermal electron source, Schottky-emission source, field emission source, etc. The electron source emits the plurality of electrons along an emission axis.

At 304, the plurality of electrons are formed into a first electron beam and a second electron beam. According to the present invention, the plurality of electrons are formed into the two beams by a bifocal beamformer or a component thereof. In some embodiments, a component of the bifocal beamformer defines at least a first aperture that is configured to allow a first portion of the electrons to pass through the bifocal beamformer (i.e., the first electron beam) and a second aperture configured to allow a second portion of the electrons to pass through the bifocal beamformer (i.e., the second electron beam). Alternatively, or in addition, the bifocal beamformer may include a biprism, an amplitude-division electron beam splitter made of thin crystals or nanofabricated gratings, a beam splitting laser system, or another type of mechanism known to those skilled in the art for splitting electron beams.

At 306, the focal properties of at least one of the first electron beam and the second electron beam is modified. Specifically, according to the present invention the bifocal beamformer or a component thereof is further configured to modify the focal properties of at least one of the first electron beam and a second electron beam such that the two beams have different corresponding focal planes. In some embodiments, the focal properties and/or focal planes of both beams is adjusted. However, in other embodiments, the focal properties and/or focal planes of just one of the two beams is adjusted.

In some embodiments, the bifocal beamformer is a MEMS device that comprises a plurality of electrodes configured to, when certain voltages are applied thereto, generate an electromagnetic field pattern that applies at least quadrupole a lensing effect to one of the electron beams. In another example, where the bifocal beamformer comprises a plurality of apertures and/or cavities, the plurality of apertures and/or cavities form a pattern that creates an electromagnetic field that applies at least a quadrupole lensing effect to one of the electron beams during use of the bifocal beamformer. Such lensing effects focus, stigmate, or otherwise modify at least the electron beam such that the corresponding focal properties of the two beams are made different. In some embodiments, a quadrupole lensing effect applied by the bifocal beam former adjusts the focal properties of one of the electron beams while applying an astigmatism to the beam that causes it to be non-cylindrically symmetric (see, FIG. 4). In such embodiments, a multipole element (e.g., a stigmator) downstream of the bifocal beamformer applies a complimentary quadrupole lensing effect to the one of the electron beams to cause it to become a cylindrically symmetric beam again. Thus, downstream of such a corrector each electron beam may be cylindrically symmetric, while having different focal planes. In various setups this corrector may be placed in a focal plane of the other electron beam so that the quadrupole lensing effect is not applied to the other electron beam.

Alternatively, or in addition, the bifocal beamformer may include one or more lenses positioned or otherwise configured to modify the focal planes of the first or second electron beam. In some embodiments, the bifocal beamformer adjusts the focal properties and/or focal planes of different regions of the electrons emitted by the electron source before they are split into the first and second electron beams, such that when the electrons are split into the two electron beams, the two beams have different corresponding focal planes.

At 308, one of the electron beams is focused onto a first plane on the sample, and at 310, the other electron beam is focused on a second plane that is not at or near the sample. In various embodiments, the one of the electron beams is focused so that it passes through an aperture in the sample and/or a portion of the sample that is thin enough that the electron beam is not substantially affected by the sample. This allows the one of the electron beams to serve as a reference beam that enables diffraction electron holography.

In some embodiments, the other electron beam is focused on a plane located at least 0.1%, 1%, 10%, or 100% of the objective lens focal distance above and/or below the sample. Additionally, the two electron beams may be focused such that the diameter of one of the electron beams at the sample is at least one of 50, 100, 500, or 1000 times greater than the diameter of the other electron beam at the sample. In some embodiments, the electron beams pass through a focusing column that directs them onto their respective focus planes. The focusing column may include one or more correctors, transfer lenses, deflectors, scan coils, beam blankers, etc. necessary to enable and/or enhance the investigation of the sample.

At 312, electrons and/or emissions resultant from the electron beams interacting with the sample are detected. For example, one or more detectors positioned in the diffraction plane may detect portions of the electron beams that are transmitted through the sample, electrons diffracted by the sample, emissions from the sample, or a combination thereof. Specifically, an interference pattern of the two electron beams is detected. In some embodiments, the interfere pattern is detected in the diffraction plane.

At 314, a diffraction hologram is generated is generated based on the interference pattern of the two electron beams. Because the two beams are mutually coherent, the one of the electron beams has a known phase and acts as a reference beam to enable the phase of the electrons diffracted by the sample, allowing both the phase and the amplitude of the diffraction pattern to be determined. As discussed above, this process can be used to determine the phase and amplitude of the diffraction peaks in the interference pattern/diffraction hologram, which can in turn be used to determine the structure and/or other crystallographic information about the crystal, even where no prior information was known about the crystal.

Moreover, the diffraction hologram can then be used to retrieve the specimen exit wave function (e.g., both amplitude and phase). In some embodiments, this specimen wave function can then be used to determine the crystal lattice (i.e., crystal structure) and/or a hologram image of the sample structure.

In an alternate or supplemental process step, the phase information of the specimen exit wave function may be determined separate from the holography analysis discussed above. For example, where the beam that is focused so that it passes through the sample is applied multiple times with different known relative phase shifts (e.g., by shifting, defocusing, or causing other kinds of aberrations to one of the two beams using, e.g., the bifocal beamforming MEMS device, etc.), the resulting intensity patterns can be recorded and then used to derive the relative phase of the wave at the detector/in the diffraction plane. For example, a phase difference cp between the detected interference pattern/diffraction hologram and the reference beam may be according to the relationships:

$$\tan\varphi = \frac{Ls_b^2 - s_a^2}{Lc_b s_b - c_a s_a}; L = \frac{I_2 - I_1}{I_3 - I_1}; s_a = \sin(\alpha/2); \quad (1)$$
$$c_a = \cos(\alpha/2); s_b = \sin(\beta/2); c_b = \cos(\beta/2);$$

where $I_1$, $I_2$, and $I_3$ are the measured intensities for 3 different phase shifts between the two beams, a is the phase shift difference of one of the beams between a first measurement and a second measurement, and $\beta$ is the phase shift difference of one of the beams between the first measurement and a third measurement.

Figure 4:
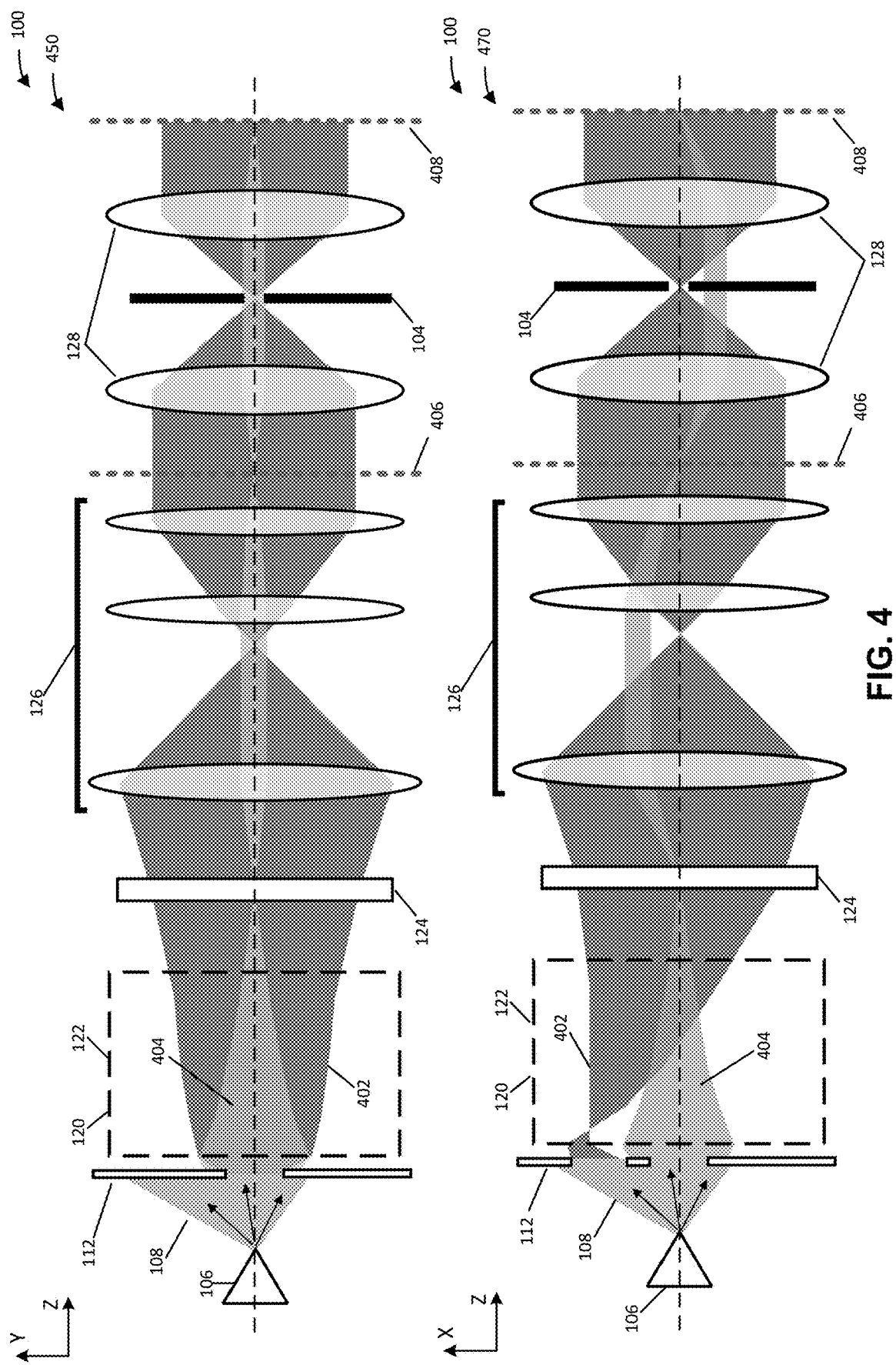
FIGS. 4, 5, and 6 are illustrations of the optical performance of a bifocal multibeam systems according to the present invention.
Figure 5:
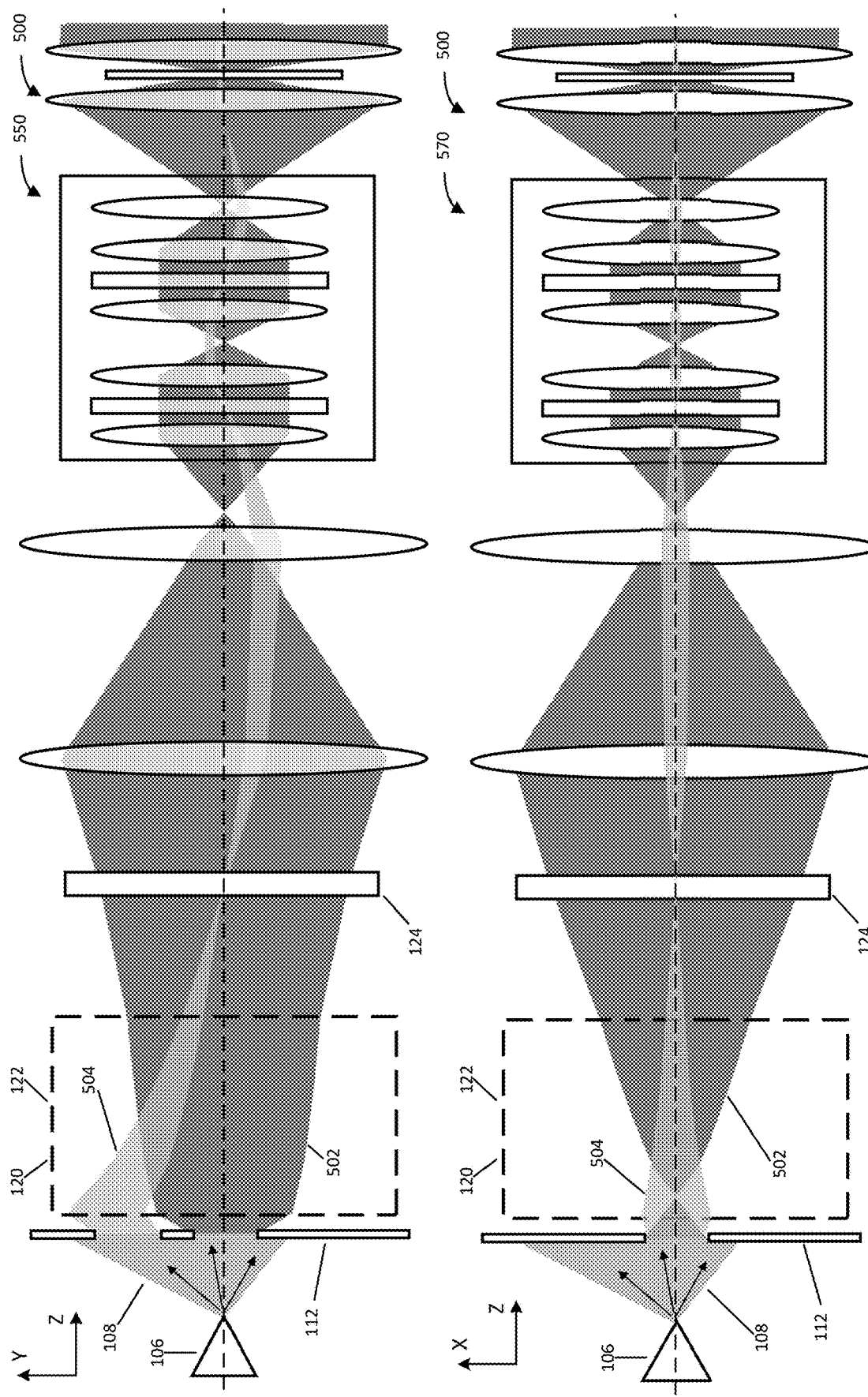
Figure 6:
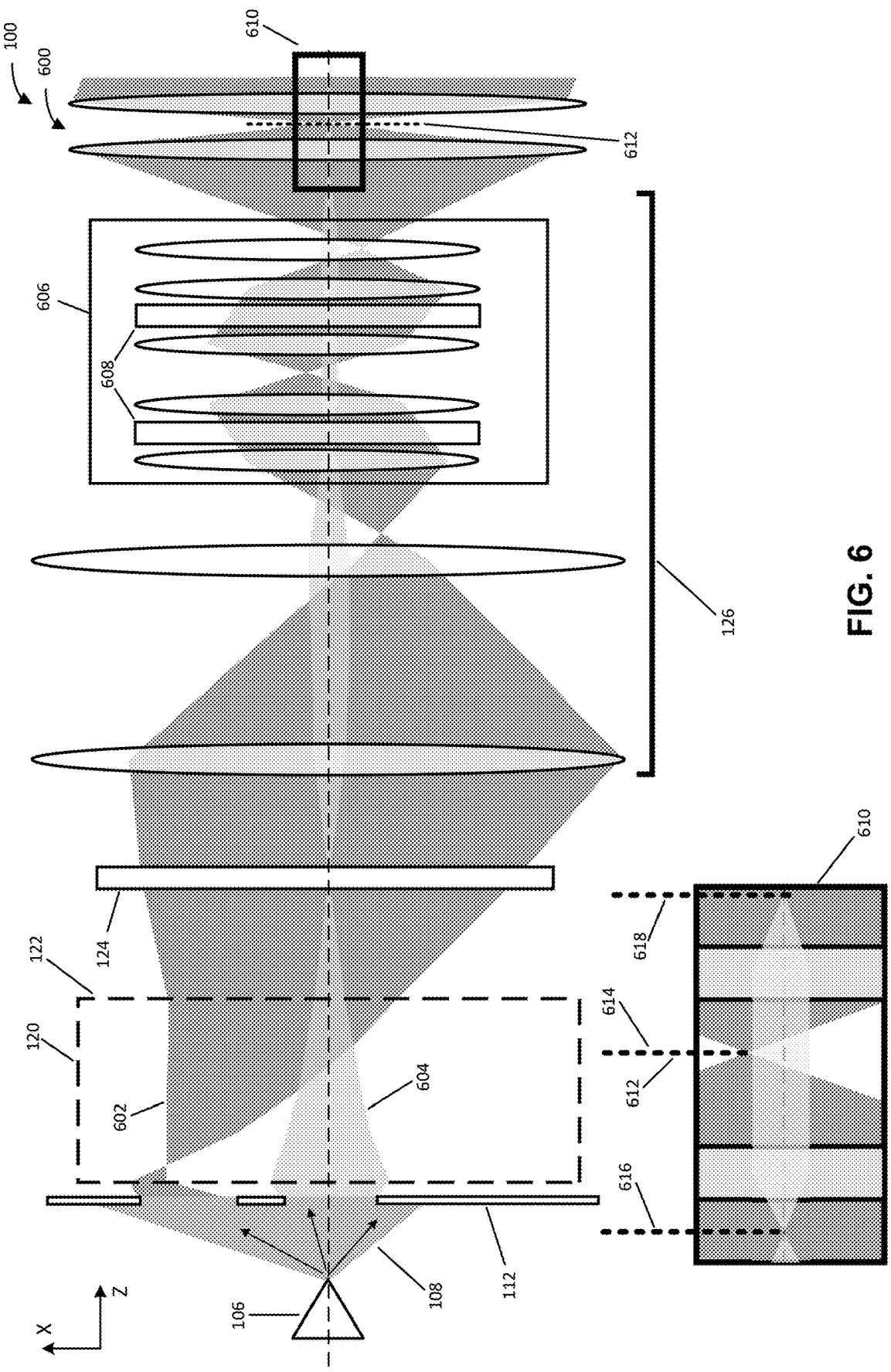

FIGS. 4-6 are illustrations of the optical performance of a bifocal multibeam system(s) 100 according to the present invention. FIG. 4 shows example beam paths of example bifocal multibeam system 400 setup to conduct electron diffraction holography. Specifically, FIG. 4 shows beam paths for an example bifocal multibeam system 400 where a quadrupole lensing effect is applied to a non-axial first electron beam 402, and no quadrupole lensing effect is applied to an axial second electron beam 404. FIG. 4 shows example beam paths of the axial first electron beam 402 and the non-axial second electron beam 404 in the y-z plane 450, and the x-z plane 470.

FIG. 4 depicts an electron source 106 emitting a plurality of electrons 108 toward a bifocal beamformer 112. The bifocal beamformer 112 is illustrated as both splitting the plurality of electrons 108 into an axial first electron beam 404 and a non-axial second electron beam 402. FIG. 4 further illustrates the bifocal beamformer 112 as applying at least a quadrupole lensing effect to the non-axial first electron beam 402, which changes the focal properties of the non-axial first electron beam 402. FIG. 4 shows how in some embodiments the at least the quadrupole lensing effect applies a stigmation to the non-axial first electron beam 402. That is, FIG. 4 illustrates how the quadrupole lensing effect may apply a first lensing effect to the non-axial first electron beam 402 in one meridional plane (i.e., a negative lensing effect in the x-z plane 450) and a second, different lensing effect to the non-axial first electron beam 402 in a perpendicular meridional plane (i.e., a positive lensing effect in the y-z plane 470). FIG. 4 shows how these two different lensing effects in different planes cause the non-axial first electron beam 402 to no longer be a cylindrically symmetric beam (i.e., the radius of the beam in the x-z plane is the not same as the radius of the beam in the y-z plane).

FIG. 4 also illustrates the example bifocal multibeam system 400 as including a multipole element 124 that is positioned at a focal plane of the axial second electron beam 404 and is configured to apply at least a quadrupole lensing effect to the non-axial first electron beam 402 such that it is once again a cylindrically symmetric beam (i.e., the radius of the beam in the x-z plane is the same as the radius of the beam in the y-z plane). Because the corrector is positioned in a plane where the axial second electron beam 404 is focused to a point, the effect of the multipole element 124 on the axial second electron beam 404 is minimized. In various embodiments, the column deflectors and/or the tilt of sample holder can be used to tune the tilt and/or shift of the beams with respect to sample, while preserving the mutual tilt angle between the two beams. FIG. 4 further shows the multipole element 124 as generating a dipole electromagnetic field that applies a deflection to each of the first electron beam 402 and the second electron beam 404. FIG. 4 illustrates this force as causing the first electron beam 402 to become an axial beam downstream of the multipole element 124 and causing the second electron beam 404 to become a non-axial beam downstream of the multipole element 124.

FIG. 4 shows the first electron beam 402 as being a reference beam that passes through an aperture in the sample 104, and the second electron beam 404 as being a TEM beam that is incident on the sample 104. The TEM beam has a front focal plane 406 upstream of the sample 104 and a back focal plane 408 downstream of the sample 104. The back focal plane 408 corresponds to the diffraction plane 408. FIG. 4 also shows the objective lens 128 as being a TEM objective lens comprising a pre-specimen component and a post specimen component.

FIG. 5 shows example beam paths of example bifocal multibeam system 500 where a quadrupole lensing effect is applied to an axial first electron beam 502, and no quadrupole lensing effect is applied to a non-axial second electron beam 504. Specifically, FIG. 5 shows example beam paths of the axial first electron beam 502 and the non-axial second electron beam 504 in the y-z plane 550, and the x-z plane 570.

Figure 9:
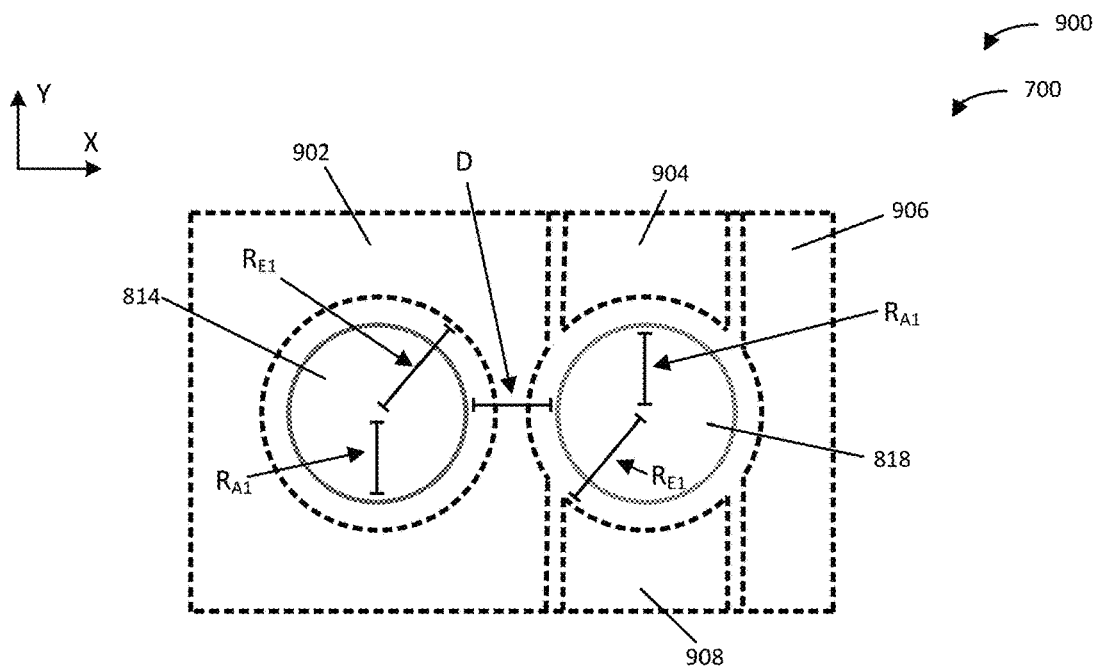
FIG. 9 illustrates a top down schematic view of an example embodiment of MEMS device that comprises four electrodes.

FIG. 5 depicts an electron source 106 emitting a plurality of electrons 108 toward a bifocal beamformer 112. The bifocal beamformer 112 is illustrated as both splitting the plurality of electrons 108 into an axial first electron beam 902 and a non-axial second electron beam 904. FIG. 9 further illustrates the bifocal beamformer 112 as applying at least a quadrupole lensing effect to the axial first electron beam 902, which changes the focal properties of the axial first electron beam 902. Specifically, FIG. 5 shows how in some embodiments the at least the quadrupole lensing effect applies a first effect to the axial first electron beam 502 in one meridional plane (i.e., a negative lensing effect in the x-z plane) and a second, different effect to the axial first electron beam 502 in a perpendicular meridional plane (i.e., a positive lensing effect in the y-z plane).

FIG. 5 also illustrates the example bifocal multibeam system 500 as including a multipole element 124 that is positioned at a focal plane of the non-axial second electron beam 504 and is configured to apply at least a quadrupole lensing effect to the axial first electron beam 502 such that it is once again a cylindrically symmetric beam. Because the corrector is positioned in a plane where the non-axial second electron beam 504 is focused to a point, the effect of the corrector on the non-axial second electron beam 504 is minimized. In various embodiments, the column deflectors and/or the tilt of sample holder can be used to tune the tilt of the electron beams with respect to sample, while preserving the mutual tilt angle between the two beams. In various embodiments, column deflectors and/or the tilt of a sample holder can be used to tune the tilt of the electron beams with respect to sample, while preserving the mutual tilt angle between the two beams.

FIG. 6 shows example beam paths of bifocal multibeam system 600 where at least a quadrupole lensing effect is applied to a non-axial reference electron beam 602 and an axial electron TEM beam 604. FIG. 6 depicts an electron source 106 emitting a plurality of electrons 108 toward a bifocal beamformer 112. The bifocal beamformer 112 is illustrated as both splitting the plurality of electron 108 into a non-axial reference electron beam 602 and an axial electron TEM beam 604. FIG. 6 further illustrates the bifocal beamformer 112 as applying at least a quadrupole lensing effect to the non-axial reference electron beam 602, which changes the focal properties of the non-axial reference electron beam 602.

In some embodiments, a result of the quadrupole lensing effect is that the non-axial reference electron beam 602 is no longer a cylindrically symmetric beam. A multipole element 124 (e.g., a multipole, a stigmator, etc.) for correcting one or more astigmatisms and/or causing the non-axial reference electron beam 602 to be cylindrically symmetric is shown in FIG. 1 as being positioned at a focal plane of the axial electron TEM beam 604. For example, the multipole element 124 may apply at least a quadrupole lensing effect to the non-axial reference electron beam 602 such that it becomes cylindrically symmetric again. Because the corrector is positioned in a plane where the axial reference electron beam 602 is focused to a point, the effect of the corrector on the beam is minimized.

The focusing column 126 is shown as including a hexapole corrector 606. In the depicted embodiment, the hexapoles 608 of the hexapole corrector 606 are shown as being positioned at focal planes of the axial electron TEM beam 604. The focusing column 126 is shown as focusing the non-axial reference electron beam 602 onto a specimen focal plane 612. To illustrate this, FIG. 6 depicts an inset 610 that shows a focal plane 614 of the on-axial reference electron beam 602 as coinciding with the specimen focal plane 612. The inset 610 further shows that the focusing column 126 as focusing the axial electron TEM beam 604 such that it has a focal plane 616 upstream of the specimen focal plane 612 and a focal plane 618 downstream of the specimen focal plane 614.

Figure 7:
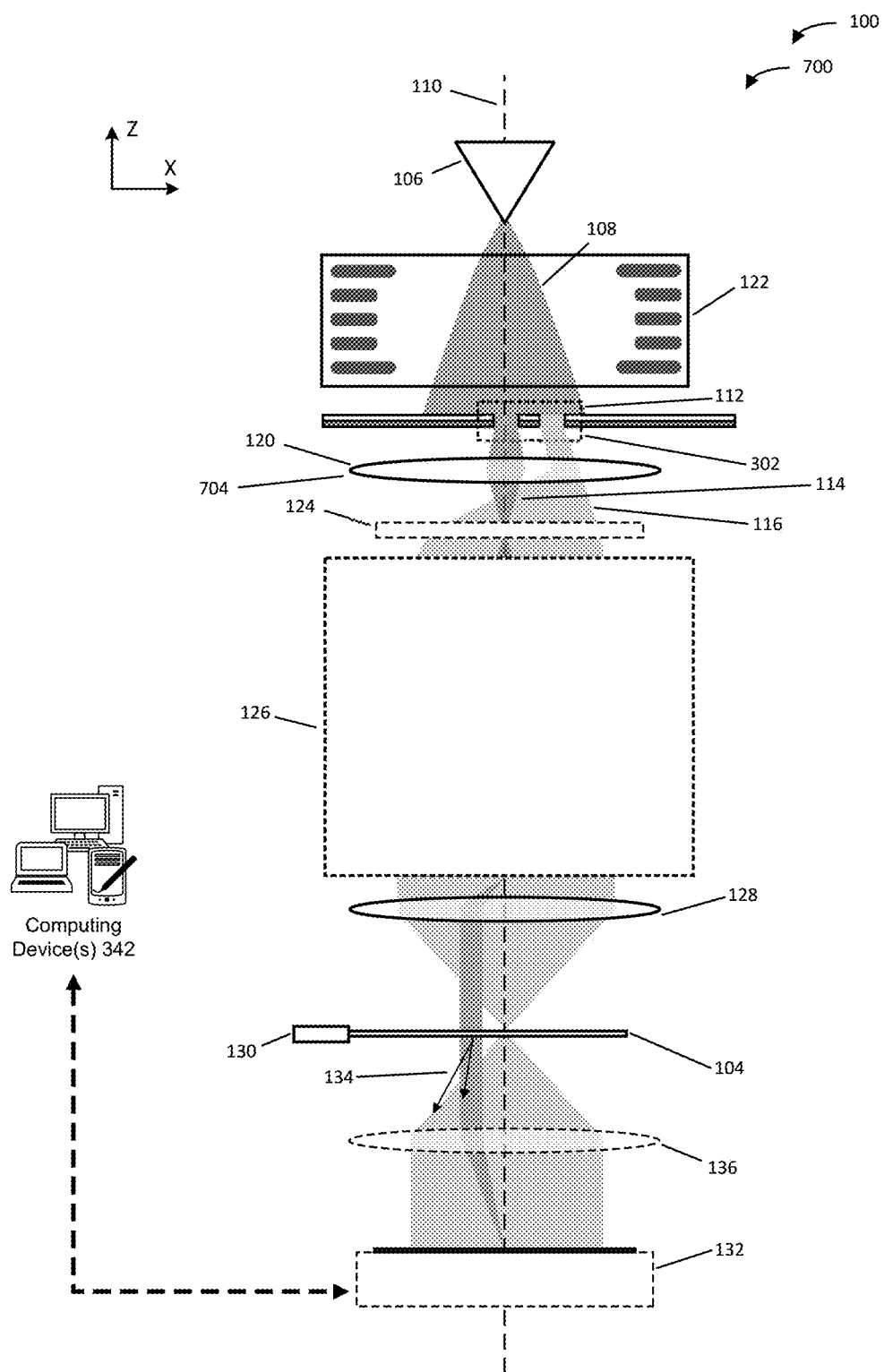
FIG. 7 illustrates example bifocal multibeam systems for investigating a sample where the bifocal beamformer comprises a MEMS device.

FIG. 7 is an illustration of an example embodiment 700 of bifocal multibeam system(s) 100 for investigating a sample 104 where the bifocal beamformer comprises a MEMS device 702.

The example bifocal multibeam system(s) 700 includes an electron source 106 that emits a plurality of electrons 108 along an emission axis 110 and towards an accelerator 120. The accelerator 120 accelerates/decelerates, focuses, and/or directs the first electron beam 114 and the second electron beam 116 towards a bifocal beamformer 112. FIG. 7 illustrates the accelerator 120 as being positioned upstream of bifocal beamformer 112, as discussed above, in other embodiments the bifocal beamformer 112 may be positioned between the electron source 106 and the accelerator 120.

In example bifocal multibeam system(s) 700, the bifocal beamformer 112 corresponds to a MEMS device 702. The MEMS device 702 defines a first aperture and a second aperture that are each configured to allow a portion of the plurality of electrons 108 to pass through the MEMS device 702. In this way, the first aperture and the second aperture split the plurality of electrons 108 into the first electron beam 114 and the second electron beam 116, respectively. FIG. 7 illustrates the first electron beam 114 as being an axial beam.

The MEMS device 702 further comprises a plurality of electrodes that are configured such that, when certain voltages are applied thereto, the electrodes generate a quadrupole electromagnetic field that applies at least a quadrupole lensing effect (i.e., dipole field, quadrupole field, hexapole field, octupole field, etc.) to the second electron beam 116. The quadrupole lensing effect focuses, stigmatizes, or otherwise modifies at least the second electron beam 116 such that the corresponding focal properties of the beams are made different. In some embodiments, the electrodes are configured such that the first electron beam 114 is not affected by the electromagnetic field generated by the electrodes and/or such an effect is reduced. Alternatively, or in addition, a portion of the electrodes may generate an electromagnetic field that applies a different lensing effect to the first electron beam 114 and the second electron beam 116.

FIG. 7 illustrates the MEMS device 702 as being positioned upstream of focusing component 120 that is configured to apply a lensing action that focuses at least one of the first electron beam 114 and the second electron beam 116. In the example bifocal multibeam system(s) 700 shown in FIG. 7, the focusing component corresponds to lens 120 that focuses, and/or directs the first electron beam 114 and the second electron beam 116 towards a focusing column 126. However, in other embodiments the accelerator 122 may be positioned between electron source 106 and the MEMS device 702, and the accelerator 122 may replace or augment the lens 704 (as illustrated in FIG. 1).

The focusing column 126 and the objective lens 128 focus the electron beams 114 and 116 so that they are incident on sample 104. Specifically, FIG. 7 illustrates the focusing column 126 focusing the second electron beam 116 so that is focused on the sample 104 and the first electron beam 114 such that it is not focused on the sample 104. FIG. 7 shows the second electron beam 116 as being a reference beam that passes through a thin portion of the sample 104, and the first electron beam 114 as being a TEM beam that is incident on the sample 104.

In some embodiments, the focal planes the first electron beam 114 and the second electron beam 116 are modified such that one of the beams is focused at a plane at or near the sample 104 and the other electron beam is focused at a plane which is located at least 0.1%, 1%, 10%, or 100% of the objective lens focal distance above and/or below the sample 104. Alternatively or in addition, the focal planes of the first electron beam 114 and the second electron beam 116 may be modified such that the diameter of one of the electron beams at the sample 104 is at least one of 5, 10, 20, 50, 100, 500, or 1000 times greater than the diameter of the other electron beam at the sample.

Figure 8:
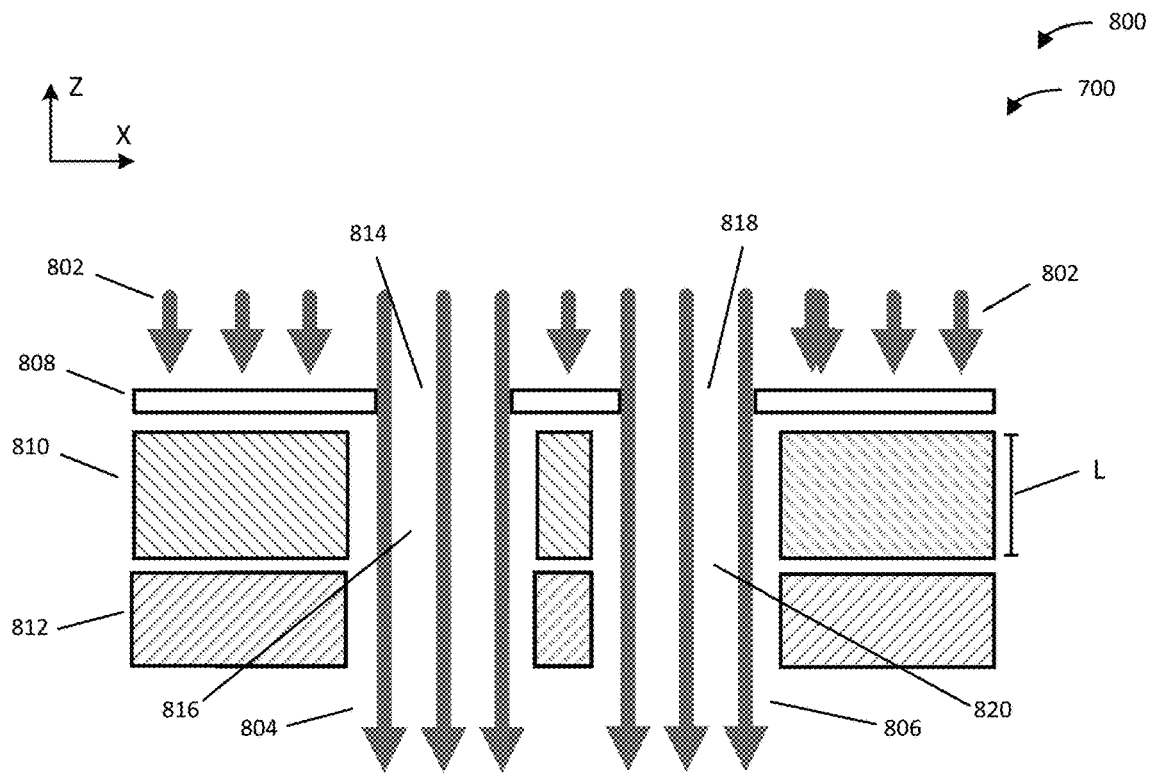
FIG. 8 illustrates an example MEMS device according to the present invention.

FIG. 8 shows a cross section of an example embodiment 800 of MEMS device 700 according to the present invention. Specifically, FIG. 8 illustrates a cross section of a MEMS device 700 configured to split a plurality of electrons 802 into the first electron beam 804 and the second electron beam 806, and generate an electromagnetic field pattern that applies at least a quadrupole lensing effect to the second electron beam 806. The at least the quadrupole lensing effect causes the first electron beam 804 and the second electron beam 806 to have different focal properties. For example, the quadrupole lensing effect may apply a positive lensing effect in one meridional plane (e.g. an y-z plane) and a negative lensing effect in a perpendicular meridional plane (e.g., a x-z plane), causing a different change to the focal properties in each of the two meridional planes. In such embodiments, another system component (e.g., a corrector or stigmator) may be included downstream of the bifocal beamformer 700 to apply another quadrupole lensing effect to make the beam cylindrically symmetric again.

FIG. 8 illustrates MEMS device 700 as including a surface layer 808, an electrode layer 810, and an optional shielding layer 812. In FIG. 8, the surface layer 808 is shown as comprising a thin material (e.g., a foil) upon which the electrons 802 are incident. However, a person having skill in the art would understand that in other embodiments, the surface layer 808 may not be a correspond to separate component layer, but rather correspond to an upper surface of one or more components of the MEMS device 700 upon which the electrons 802 are incident.

The surface layer 808 defines a first entrance 814 to a first aperture 816 and a second entrance 818 to a second aperture 820. In some embodiments, the first aperture 814 is an axial aperture (i.e., positioned on the emission axis of the electrons 802) and the second aperture 818 is a non-axial aperture. In such embodiments, the first electron beam 804 is an axial beam. The first entrance 814 allows a first portion of the electrons 802 (i.e., the first electron beam 804) to pass into the first aperture 816 and through the MEMS device 700. Similarly, the second entrance 818 allows a second portion of the electrons 402 (i.e., the second electron beam 806) to pass into the second aperture 820 and through the MEMS device 700. The surface layer 808 inhibits the ability of the remaining portions of electrons 802 to pass into and/or through the MEMS device 700.

The electrode layer 810 comprises a plurality of microelectrodes that are shaped, positioned, or otherwise configured such that when corresponding voltages are applied to the one or more electrodes, the one or more electrode generate electromagnetic field patterns that apply a lensing effect to one or both of the first electron beam 804 and the second electron beam 806. The lensing effect is such that the focal properties of the two beams are modified such that they have different corresponding focal properties. One or more of the magnitude of the voltages applied to the electrodes, the shape of the electrodes, and the thickness (L) of the electrodes can be modified to change the strength of the generated electromagnetic field patterns. According to the present invention, the electrodes in the electrode layer 810 are configured such that they generate at least a quadrupole electromagnetic field pattern applies at least a quadrupole lensing effect (i.e., dipole field, quadrupole field, hexapole field, octupole field, etc.) to the second electron beam 806. In some embodiments, the electromagnetic field pattern may also apply dipole fields to one or both of the first electron beam 804 and the second electron beam 806. Such dipole fields may cause at least one of the electron beams to be deflected in a direction perpendicular to the emission axis.

FIG. 8 also illustrates the MEMS device 700 as including an optional shielding layer 812 that is opposite the surface layer 808, and which is configured to at least partially insulate the first electron beam 814 from the at least quadrupole lensing effects applied to the second electron beam 816.

Figure 10:
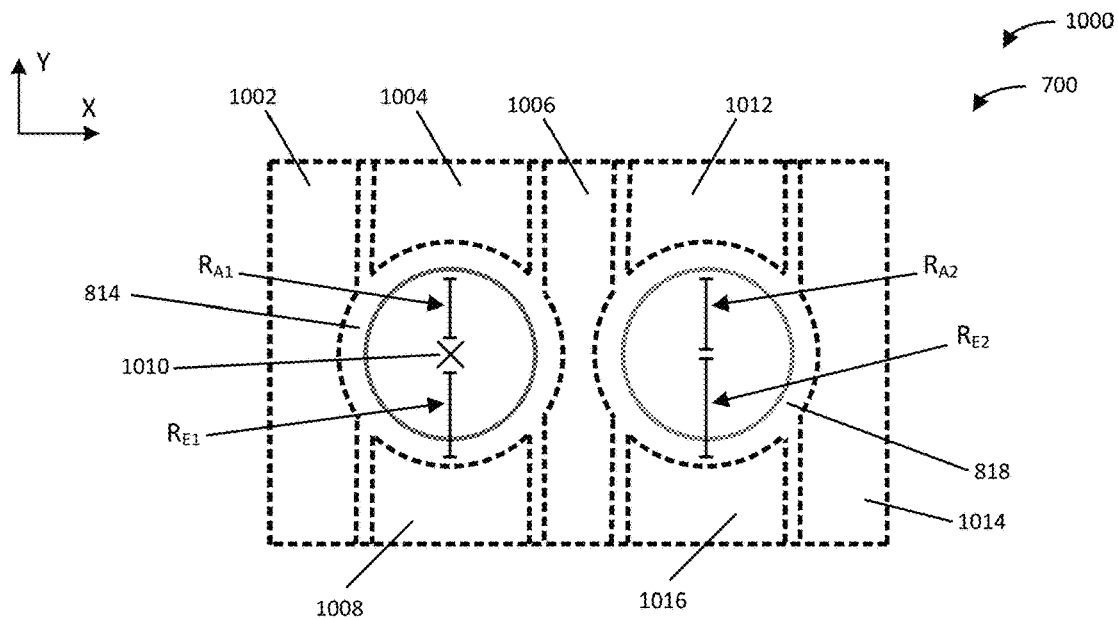
FIG. 10 illustrates a top down schematic view of an example embodiment of MEMS device that comprises seven electrodes.

FIG. 9 shows top down schematic view of an example embodiment 900 of MEMS device 700 that comprises four electrodes. FIGS. 9 and 10 illustrate in solid lines the first entrance 814 and second entrance 818 as defined by surface layer 808 in solid lines. Additionally, FIGS. 9 and 10 illustrate the components of the electrode layer 810 in dashed lines. A person having skill in the art would recognize that the dashed lines do not represent the exact shape, but rather indicate general outlines electrodes in the electrode layer 810.

FIG. 9 shows the radius $R_{A1}$ of the first entrance 814 as being lesser than the radius $R_{E1}$ of the first aperture as at least partially defined by electrode 902. In an embodiment of example MEMS device 900, the radius $R_{A1}$ may be at or around 10 μm and the radius $R_{E1}$ may be at or around 14 μm or greater. The radius $R_{A2}$ of the second entrance 818 is shown in FIG. 9 as being lesser than the radius $R_{E2}$ of the second aperture as at least partially defined by electrodes 902, 904, 906, and 908. However, in other embodiments one or both of radius $R_{E1}$ and radius $R_{A1}$ and/or radius $R_{E2}$ and radius $R_{A2}$ may be the same. The example embodiment 900 is further shown as having the radius $R_{A1}$ and the radius $R_{A2}$ as being equal and/or approximately equal, however this is not required for all embodiments. The first entrance 814 and the second entrance 818 are separated by the distance D.

During use of the example MEMS device 900, voltages may be applied to one or more of the electrodes 902-908 such that the electrodes generate an electromagnetic field that applies at least a quadrupole lensing effect to the second electron beam. In some embodiments, one or more of the electrodes may be grounded. For example, the example MEMS device 900 may generate an electromagnetic field that applies at least a quadrupole lensing effect to the second electron beam when a first voltage V1 is applied the electrode 904, a second voltage V2 is applied to electrode 908, and electrodes 902 and 906 are grounded. In various embodiments, V1 and V2 may each be greater than −20V and less than 20V, however larger voltages can also be used.

FIG. 10 shows top down schematic view of an example embodiment 1000 of MEMS device 700 that comprises seven electrodes. FIG. 10 shows the radius $R_{A1}$ of the first entrance 814 as being lesser than the radius $R_{E1}$ of the first aperture as at least partially defined by electrodes 1002, 1004, 1006, and 1008. FIG. 10 illustrates the first aperture 814 as being an axial aperture through which the emission axis 1010 of the plurality of electrons passes.

The radius $R_{A2}$ of the second entrance 818 is also shown in FIG. 10 as being lesser than the radius $R_{E2}$ of the second aperture as at least partially defined by electrodes 1006, 1012, 1014, and 1016. However, in other embodiments one or both of radius $R_{E1}$ and radius $R_{A1}$ and/or radius $R_{E2}$ and radius $R_{A2}$ may be the same.

During use of the example MEMS device 1000, voltages may be applied to one or more of the electrodes 1002-1008 and 1012-1016 such that the electrodes generate an electromagnetic field that applies at least a quadrupole lensing effect to the second electron beam. In some embodiments, one or more of the electrodes may be grounded. For example, the example MEMS device 1000 may generate an electromagnetic field that applies at least a quadrupole lensing effect to the second electron beam when a first set of voltages between the values of −20V and 20V are applied to electrodes 1004, 1008, 1012, and 1016, a second set of voltages between the values of −5V and 5V is applied to electrodes 1002 and 1014, and electrode 1006 is grounded.

Additionally, a person having skill in the art would understand that the dashed lines in FIGS. 9 and 10 represent example configurations of electrodes, and that experimentation would provide multiple electrode configurations (e.g., electrode size, electrode shape, quantity of electrodes, layout of electrodes, combination of voltages applied to electrodes, etc.) that cause the electrodes to generate an electromagnetic field that applies at least a quadrupole lensing effect to the second electron beam. Moreover, while each of FIGS. 5 and 6 illustrate an embodiment where the at least quadrupole lensing effect is applied to the second electron beam, in other embodiments the electrode layer may be configured to generate an electromagnetic field that applies at least a quadrupole lensing effect to the first electron beam (or both electron beams) when a corresponding set of voltages are applied to the electrodes.

Figure 11:
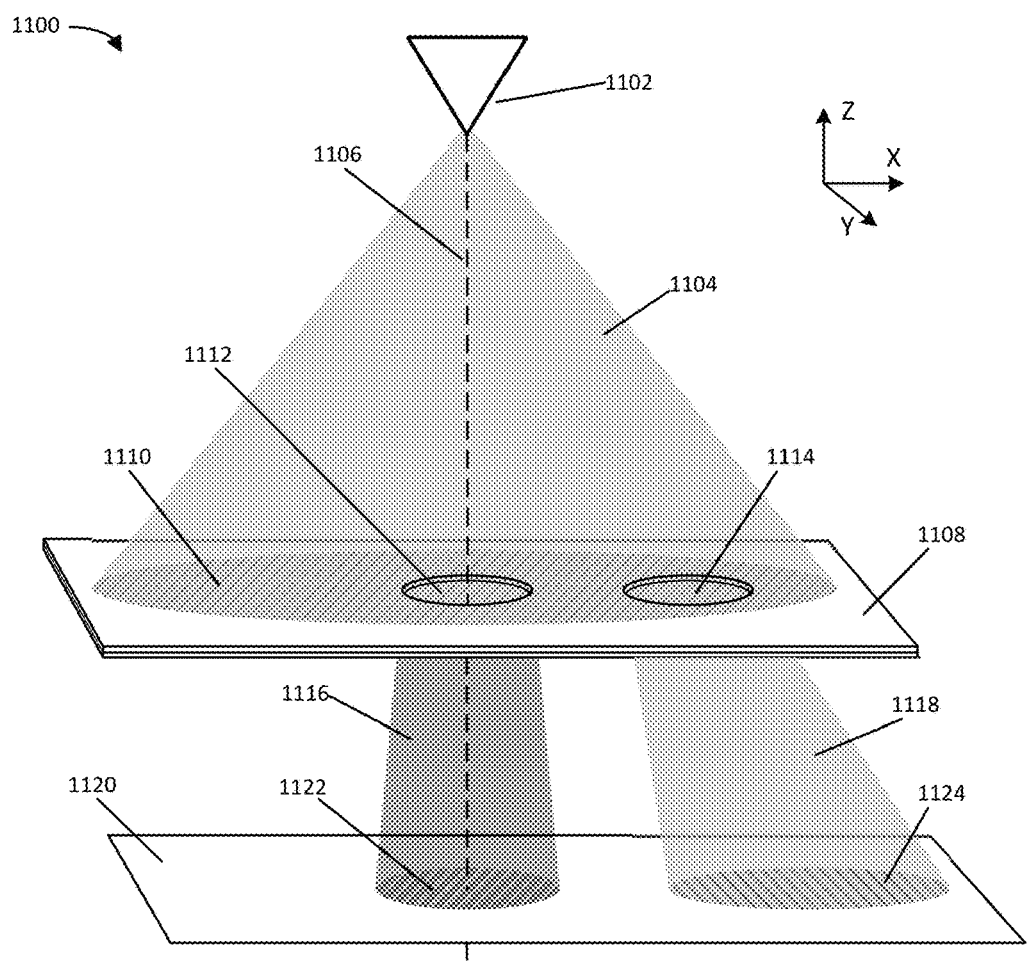
FIG. 11 illustrates the distortion of the second electron beam caused when an example embodiment bifocal beamformer causes at least a quadrupole lensing effect to be applied thereto.

FIG. 11 is an illustration 1100 of the change in focal properties of the second electron beam caused when an example embodiment bifocal beamformer causes at least a quadrupole lensing effect to be applied thereto. Specifically, FIG. 11 shows an emitter 1102 emitting a plurality of electrons 1104 along an emission axis 1106. The plurality of electrons 1104 strike the bifocal beamformer 1108 in a circular area 1110. The bifocal beamformer 1108 is shown in FIG. 11 as being a MEMS device that (i) defines a first aperture 1112 and a second aperture 1114 that split the electron beam 1104 into a first electron beam 1116 and a second electron beam 1118, respectively, and (ii) generates an electromagnetic field that applies at least a quadrupole lensing effect to the second electron beam 1118 when in use.

As illustrated in FIG. 11, in some embodiments the at least a quadrupole lensing effect causes the second electron beam 1118 to be distorted such that it (i) has a different focal properties from the first electron beam 1116, and (ii) is no longer a cylindrically symmetric beam. Specifically, FIG. 11 shows the cross-sectional areas of the first electron beam 1116 and the second electron beam 1118 in an plane 1120 downstream of the bifocal beamformer 1108, where the emission axis is normal to the plane 1120. The first electron beam 1116 is shown as having a circular (or near circular) cross section 1122 when it crosses the plane 1120, and the second electron beam 1118 is shown as having a non-circular cross section 1124 when it crosses the plane 1120. Applicant notes that these cross sections are not illustrative of the performance of all embodiments of bifocal beamformers according to the present invention, but are limited to the specific example embodiment of bifocal beamformer 1108.

Figure 12:
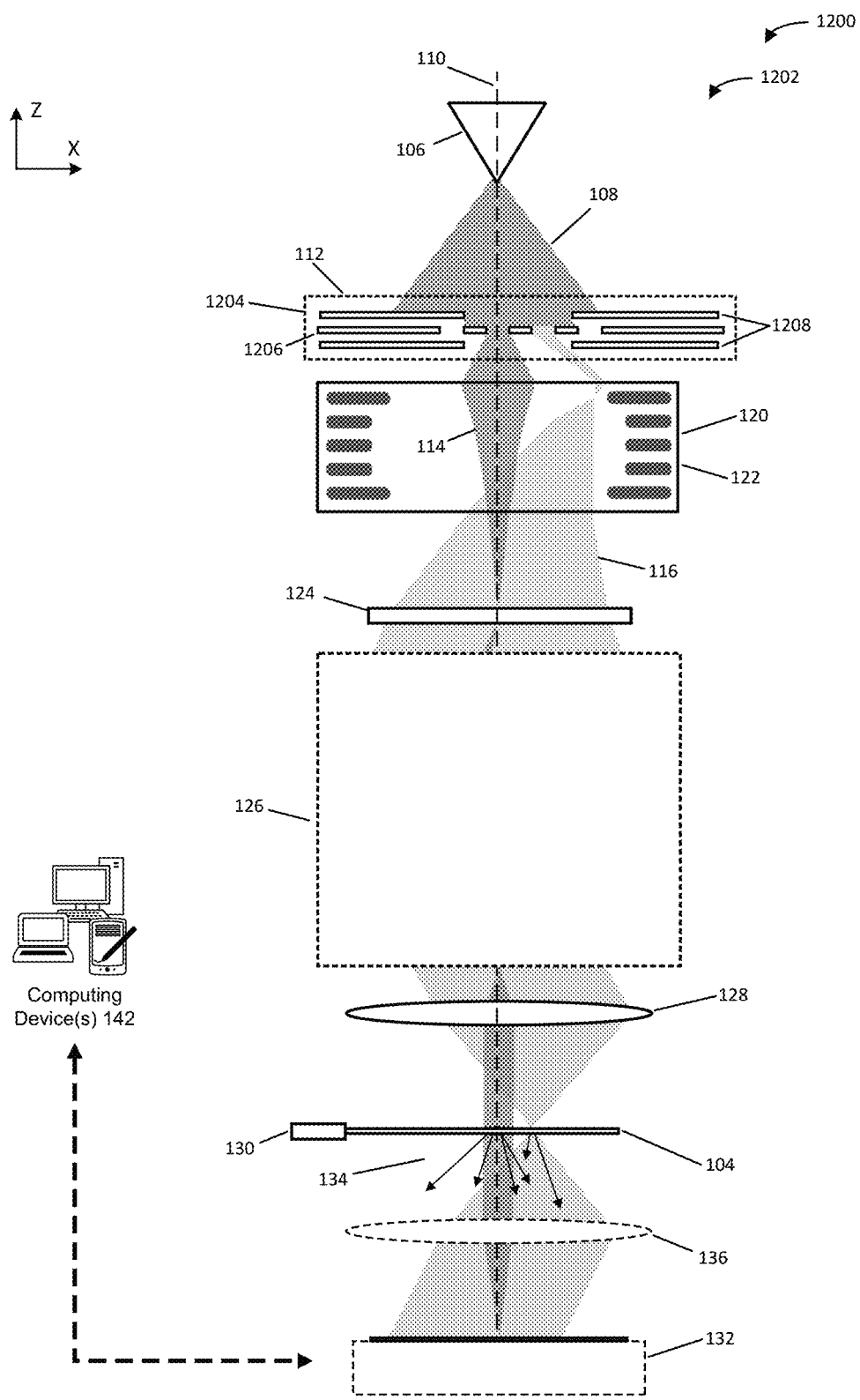
FIG. 12 illustrates example embodiments of bifocal multibeam systems for investigating a sample where the bifocal beamformer comprises an aperture lens array.

FIG. 12 is an illustration of an example embodiment 1200 of bifocal multibeam system(s) 100 for investigating a sample 104 where the bifocal beamformer comprises an aperture lens array 1203.

The example bifocal multibeam system(s) 1202 includes an electron source 106 that emits a plurality of electrons 108 along an emission axis 110 and towards an aperture lens array 1204. The aperture lens array 1204 comprises at least one aperture defining structure 1206 that defines (i) a first aperture that allows the first electron beam 114 to pass through the at least one aperture defining structure 1206, (ii) a second aperture that allows the second electron beam 116 to pass through the at least one aperture defining structure 1206, and (iii) plurality of other apertures. The first aperture, the second aperture, and the plurality of apertures collectively form a pattern that, when a voltage(s) is applied to the aperture defining structure 1206 and the electrode(s) 1208, creates an electromagnetic field that applies a lensing effect (e.g., at least a quadrupole lensing effect) to at least one of the first electron beam 114 and the second electron beam 116. The lensing effect distorts one or both of the first electron beam 114 and the second electron beam 116 such that they have different focal properties.

The aperture lens array 1204 further comprises one or more electrodes (e.g., disk electrodes) 1208. The each of the one or more electrodes 1208 generate an electric field between the corresponding electrode and the at least one aperture defining structure 1206 when a voltage is supplied thereto. Additionally, in some embodiments, one or more of the electrodes 1208 may physically block a portion of the plurality of electrons 108 from reaching the at least one aperture defining structure 106. For example, one of the electrodes 1208 may define a first aperture that allows a first portion of electrons to pass through the electrode (i.e., a first electron beam) and a second aperture that allows a second portion of electrons to pass through the electrode (i.e., a second electron beam).

FIG. 12 illustrates the bifocal beamformer 112 as being positioned upstream of focusing component 120 that is configured to apply a lensing action that focuses at least one of the first electron beam 114 and the second electron beam 116. In the example bifocal multibeam system(s) 1202 shown in FIG. 12, the focusing component corresponds to an accelerator 122 that accelerates/decelerates, focuses, and/or directs the first electron beam 114 and the second electron beam 116 towards a focusing column 126.

The focusing column 126 and the objective lens 128 focus the electron beams 114 and 116 so that they are incident on sample 104. Specifically, FIG. 12 illustrates the focusing column 126 focusing the second electron beam 116 so that is focused on a plane at or near the sample 104 and the first electron beam 114 such that it is not focused at the plane at or near the sample 104. In some embodiments, the focal properties of the first electron beam 114 and the second electron beam 116 are modified such that one of the beams is focused at a plane at or near the sample 104 and the other electron beam is focused at a plane which is located at least 0.1%, 1%, 10%, or 100% of the objective lens focal distance above and/or below the sample 104. Alternatively or in addition, the focal properties the first electron beam 114 and the second electron beam 116 may be modified such that the diameter of one of the electron beams at the sample 104 is at least one of 50, 100, 500, or 1000 times greater than the diameter of the other electron beam at the sample.

Figure 13:
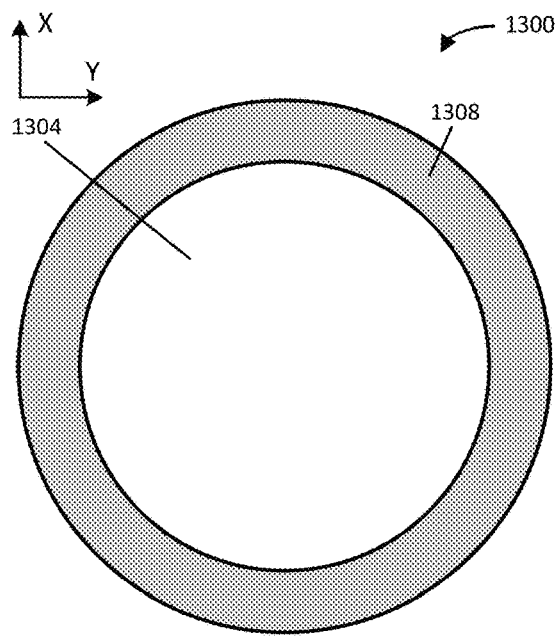
FIG. 13 illustrates an example electrode for an example aperture lens array.

FIG. 13 illustrates an example 1300 electrode 1202 for an example aperture lens array 1204. The electrode 1208 is shown in FIG. 13 as being a disk electrode 1302 that defines an aperture 1304 that allows electrons to pass through the disk electrode 1302.

Figure 14:
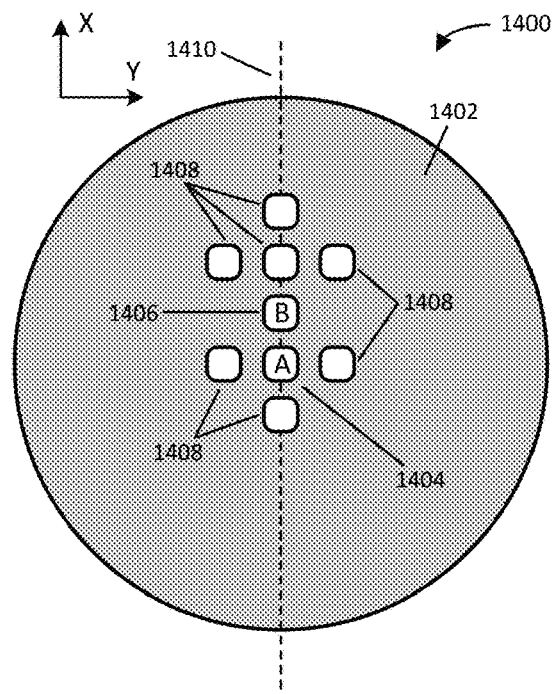
FIG. 14 illustrates an example aperture defining structure for an example aperture lens array.

FIG. 14 illustrates an example 1400 aperture defining structure 1402 for an example aperture lens array 1204. The example aperture defining structure 1402 defines (i) a first aperture 1404 that allows a first electron beam to pass through the at least one aperture defining structure 1402, (ii) a second aperture 1406 that allows a second electron beam to pass through the at least one aperture defining structure 1402, and (iii) plurality of other apertures 1408. In the example embodiment shown in FIG. 14, each of the first aperture 1404, the second aperture 1406, and three apertures 1408 are positioned along a midline 1410 of the aperture defining structure 1402.

FIG. 14 illustrates each of the plurality of other apertures 1408 as being holes that allow electrons to pass through the aperture defining structure 1402. However, in other embodiments one or more of the apertures 1408 may be cavities where the aperture defining structure 1402 defines an empty space into which electrons are allowed to enter, but which do not allow the electrons to pass through the aperture defining structure. The first aperture 1404, the second aperture 1406, and the plurality of apertures 1408 collectively form a pattern that induces an electromagnetic field that applies a lensing effect (e.g., at least a quadrupole lensing effect) to at least the second electron beam.

Figure 15:
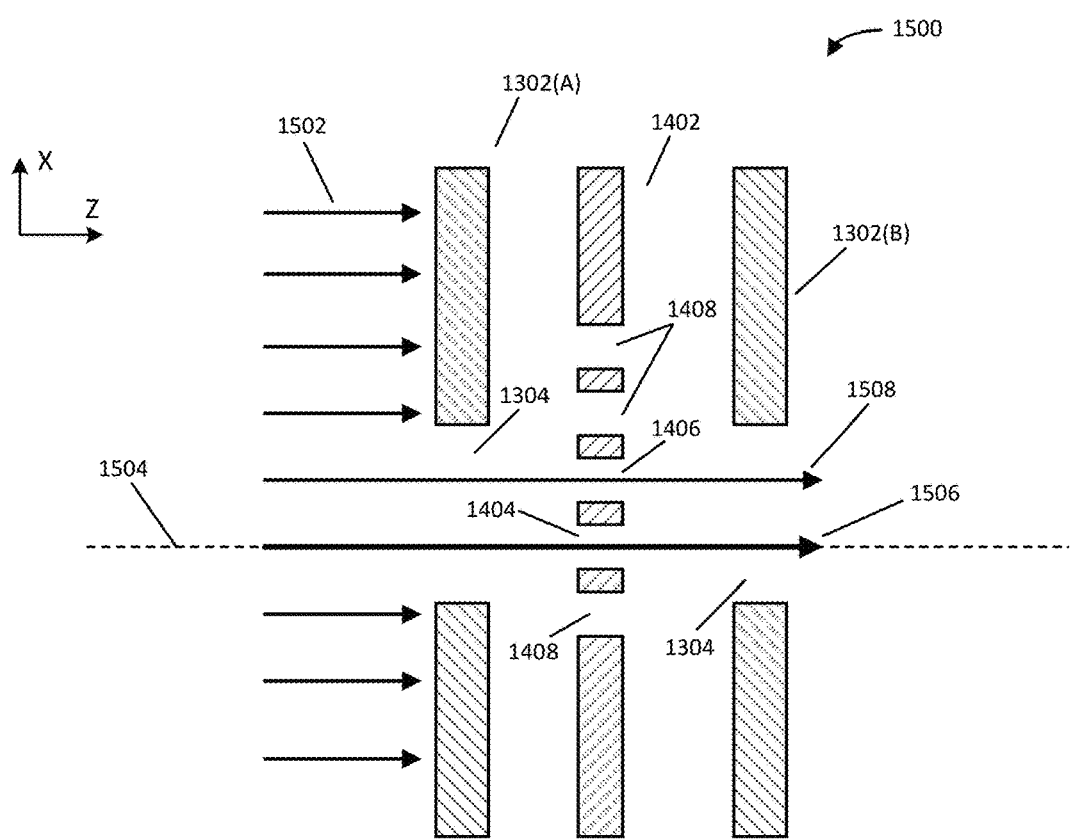
FIG. 15 illustrates a cross section of an example aperture lens array having one aperture defining structure.

FIG. 15 illustrates a cross section of an example aperture lens array 1500 having one aperture defining structure. Specifically, FIG. 15 shows a cross section of an example aperture lens array 1500 comprising the example electrode 1302 of FIG. 13 and the example aperture structure 1402 of FIG. 14, where the cut of the cross section aligns with the midline 1410 of the example aperture structure 1402.

FIG. 15 shows electrons 1502 being emitted along an emission axis toward the electrode 1302. A portion of the electrons 1502 pass through both the aperture 1304 and the first aperture 1404, becoming first electron beam 1506. Another portion of the electrons 1502 pass through both the aperture 1304 and the second aperture 1406, becoming second electron beam 1508. In some embodiments, the aperture lens array 1500 includes a second electrode positioned such that the at least one aperture defining structure 1402 is between the two electrodes. When voltages are applied to the electrode 1302(A), the electrode 1302(B), both electrodes 1302(A) and 1302(B), and/or the aperture defining structure 1402, electromagnetic fields are created between the electrodes 1302 and the aperture defining structure 1402. While FIG. 15 illustrates the aperture lens array 1500 as comprising two electrodes, in some embodiments the aperture lens array 1500 may only include one electrode (either electrodes 1302(A) or 1302(B)).

The aperture lens array 1500 is configured such that the configuration of the electrodes 1302 (i.e., one electrode, both electrodes, the positions of such electrodes, the geometry of such electrodes, etc.), the voltages (or lack of voltages) applied to individual ones of the electrodes 1302 and the aperture defining structure 1402, and the pattern that the first aperture 1404, the second aperture 1406, and the plurality of apertures 1408 collectively create an electromagnet field that creates a first lensing effect on the first electron beam and a second lensing effect on the second electron beam, where the first and second lensing effects are different. For example, in an embodiment of the present invention, the electromagnetic field may create a lensing effect (e.g., at least a quadrupole lensing effect) that causes the first electron beam 1506 and the second electron beam 1508 to have different focal properties.

In some embodiments, the electromagnetic field also deflects one or both of the first electron beam 1506 and the second electron beam 1508 away from the emission axis 1504. Also, while FIG. 15 illustrates the first electron beam 1508 as an axial beam that travels along the emission axis 1504 of the plurality of electrons 1502, this is not required in all embodiments.

Figure 16:
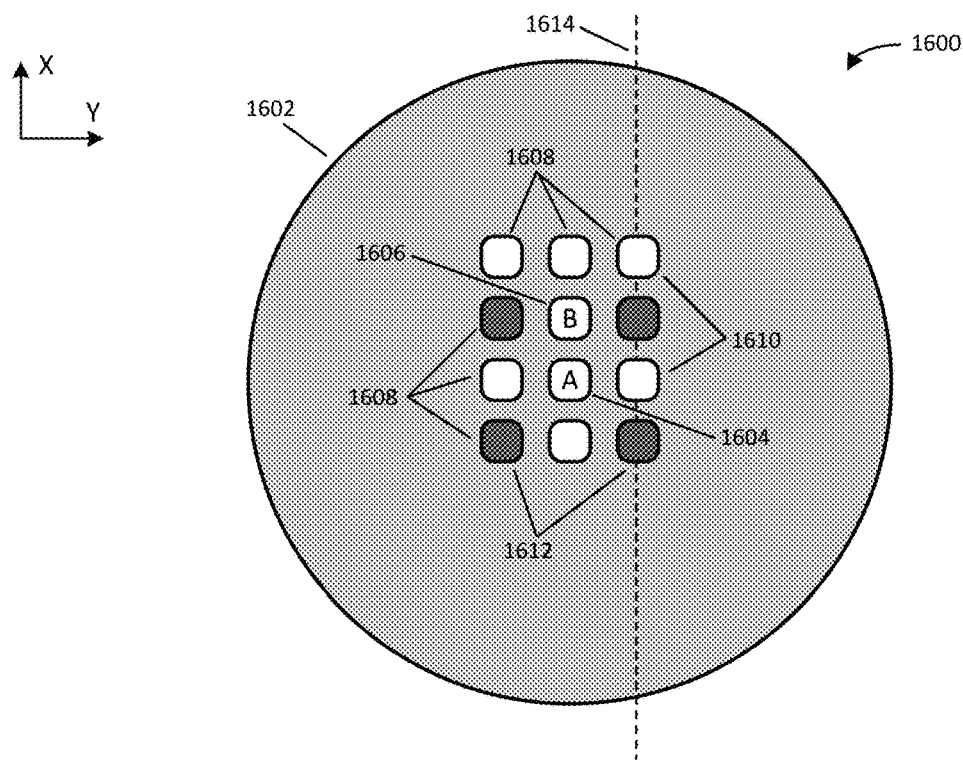
FIGS. 16-24 illustrate example central structures which can be used in the multiple aperture assembly illustrated in FIG. 23.
Figure 23:
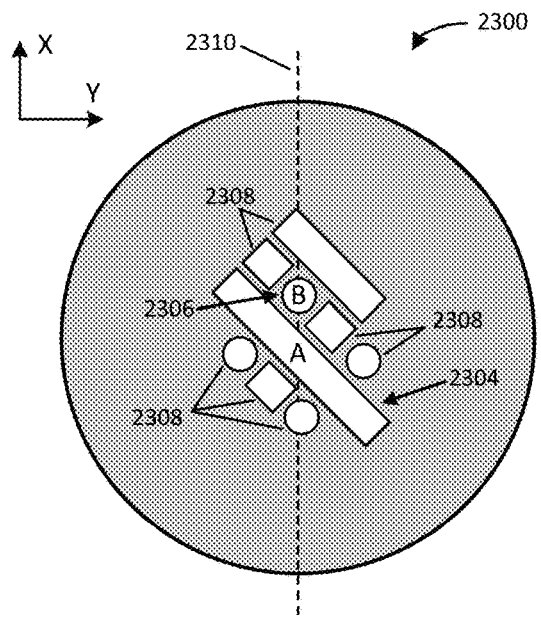
Figure 24:
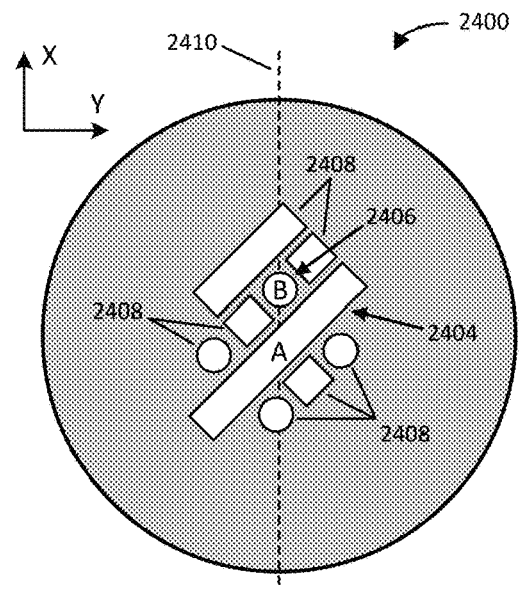
Figure 25:
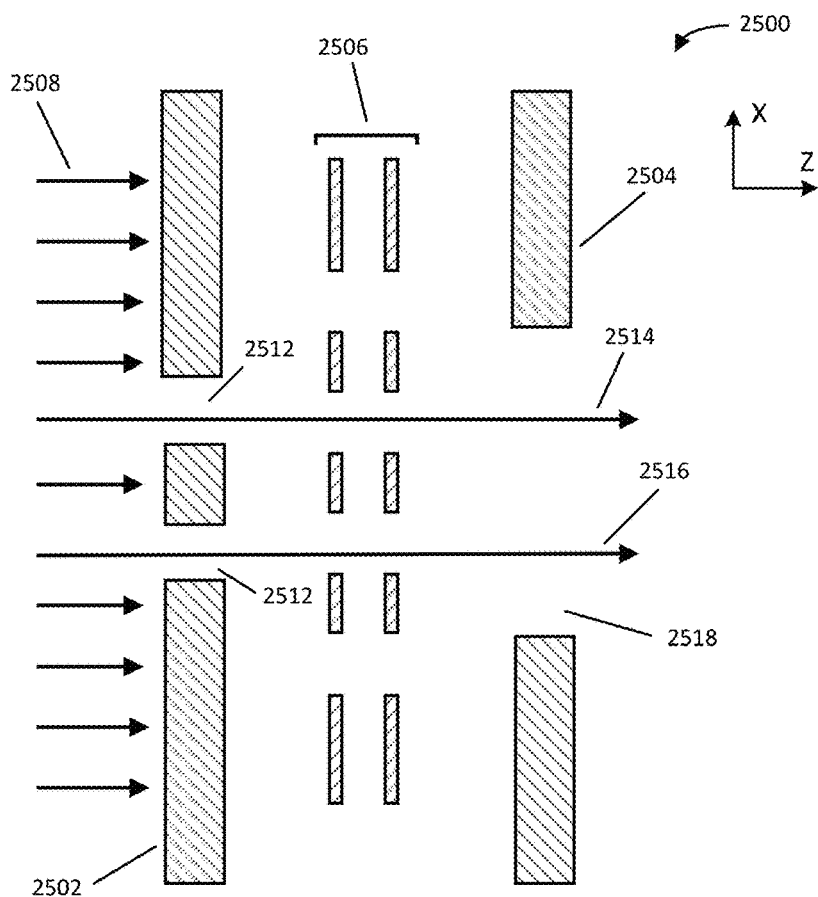
FIG. 25 illustrates a cross section of an example aperture lens array that comprises comprising a first electrode, a second electrode, and an aperture defining structure.

FIGS. 16-24 show example central structures which can be used in the multiple aperture assembly 2500 illustrated in FIG. 25. Specifically, FIG. 16 illustrates an example aperture defining structure 1600 for an example aperture lens array that includes a combination of holes and cavities. The example aperture defining structure 1602 defines (i) a first aperture 1604 that allows a first electron beam to pass through the at least one aperture defining structure 1602, (ii) a second aperture 1606 that allows a second electron beam to pass through the at least one aperture defining structure 1602, and (iii) plurality of other apertures 1608. The first aperture 1604, the second aperture 1606, and the plurality of apertures 1608 collectively form a pattern that induces an electromagnetic field that applies a lensing effect (e.g., at least a quadrupole lensing effect) to at least the second electron beam when voltages are applied to at least the aperture defining structure 1600 and electrodes 2504 and 2512 during use of the multiple aperture assembly 2500. In some embodiments, the aperture lens structure 1602 comprises a single physical component that defines each of the first aperture 1604, the second aperture 1606, and the plurality of apertures 1608. However, in other embodiments the aperture lens structure 1602 may comprise two or more component physical structures.

FIG. 16 illustrates an example embodiment in which five of the plurality of other apertures 1608 correspond to holes 1610, and four of the plurality of other apertures 1608 correspond to cavities 1612. However, in other embodiments the plurality of other apertures 1608 may comprise other combinations and/or patterns of holes and cavities, including embodiments where all of the plurality of other apertures 1608 correspond to one of holes (e.g., the aperture defining structure illustrated in FIG. 14) or cavities, exclusively. In the example embodiment shown in FIG. 16, each of the first aperture 1604, the second aperture 1606, and two other apertures 1608 are positioned along a line 1614 of the aperture defining structure 1602.

Figure 17:
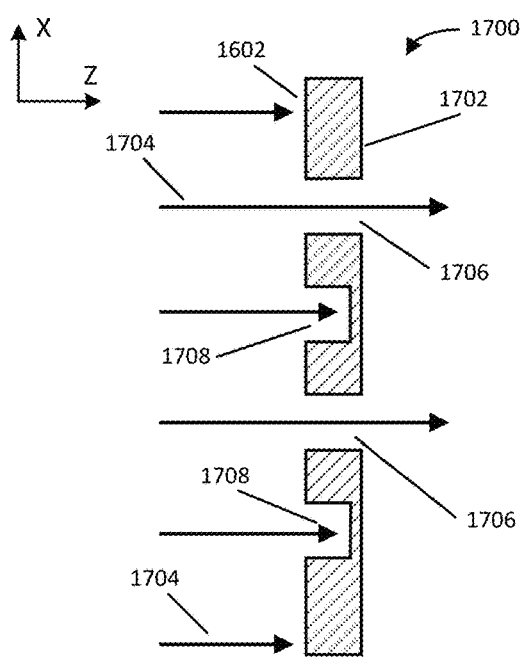

FIG. 17 illustrates a cross section 1700 of example aperture structure 1602 that comprises a single physical structure 1702. Specifically, FIG. 17 shows a cross section of an embodiment of the example aperture structure 1602 of FIG. 16, with the cut of the cross section aligning with the line 1614. A first portion of the electrons 1704 are allowed to pass through the physical structure 1702 via holes 1706. FIG. 17 further shows a second portion of the electrons 1704 are allowed to pass into cavities 1708 that prevent them from passing through the physical structure 1702.

Figure 18:
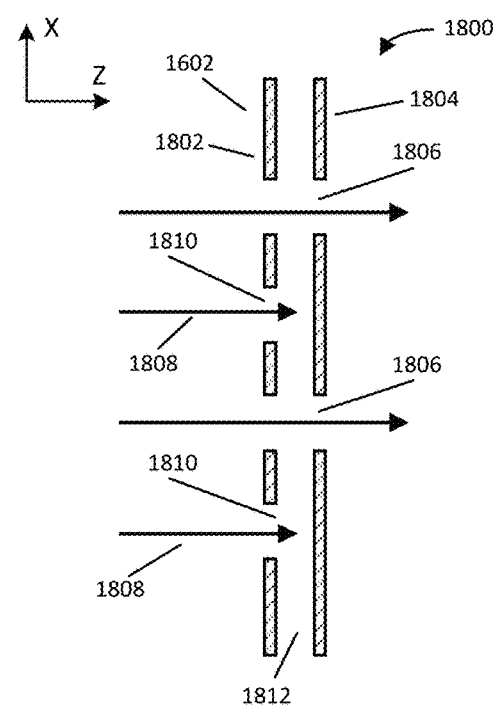

FIG. 18 illustrates a cross section 1800 of example aperture structure 1602 that comprises a first physical structure 1802 and a second physical structure 1804. Specifically, FIG. 18 shows a cross section of an embodiment of the example aperture structure 1602 where it is comprised of two structures (e.g., foils), with the cut of the cross section aligning with the line 1614. FIG. 18 illustrates holes 1806 in the example aperture structure 1602 as corresponding to complementary apertures in the first physical structure 1802 and a second physical structure 1804 that together allow a first portion of the electrons 1808 to pass through the aperture structure 1602. FIG. 18 also illustrates cavities 1810 as corresponding to apertures in the first physical structure 1802 that do not have a complimentary aperture in the second physical structure 1804. In other words, the cavities 1810 are configured such that a second portion of the electrons 1808 is allowed to pass into a space 1812 between the first physical structure 1802 and the second physical structure 1804, but are not allowed to pass through the aperture structure 1602.

Figure 19:
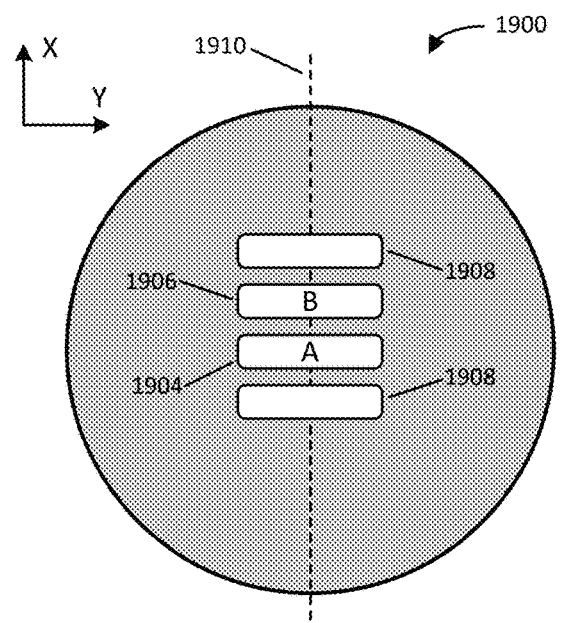
Figure 20:
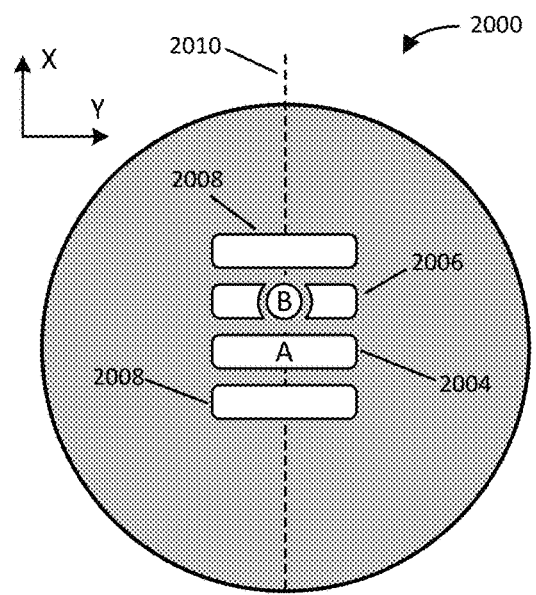

FIGS. 19 and 20 illustrate a pair of component physical structures that can be used to form an aperture defining structure 2306 in the aperture lens array 2500 illustrated in FIG. 25. Specifically, FIG. 19 illustrates an example first component physical structure 1900 of an example aperture defining structure comprising two physical structures. The example first component physical structure 1900 defines (i) a first aperture 1904 that allows a first electron beam to pass through the first component physical structure 1900, (ii) a second aperture 1906 that allows a second electron beam to pass through first component physical structure 1900, and (iii) plurality of other apertures 1908. Each of these apertures are illustrated as having a rectangular geometry (e.g., a long slot). Such rectangular apertures are configured to create a cylindrical lensing effect on electrons passing through them during use of the example aperture defining structure. In the example embodiment shown in FIG. 19, each of the first aperture 1904, the second aperture 1906, and two apertures 1908 are positioned along a midline 1910 of the first component physical structure 1900.

FIG. 20 illustrates an example second component physical structure 2000 of an example aperture defining structure comprising two physical structures. The example second component physical structure 2000 defines (i) a first aperture 2004 that allows a first electron beam to pass through the second component physical structure 2000, (ii) a second aperture 2006 that allows a second electron beam to pass through second component physical structure 2000, and (iii) plurality of other apertures 2008. Apertures 2004 and 2008 are shown as having a rectangular geometry, similar to the apertures defined by the first component physical structure 1900 illustrated in FIG. 19. The second aperture 2006 is illustrated in FIG. 20 as combining both a rectangular geometry and a circular geometry. In other words, the second aperture 2006 is shown as being a circular aperture centrally positioned and overlaid with an aperture having a rectangular geometry. This combination of the geometry of the second aperture 1906 and the second aperture 2006 cause a net quadrupole lensing effect to be applied to the electron beam B as it passes through the second apertures 1906 and 2006. Similarly, the geometries of the first aperture 1904 and the first aperture 2004 cause a no net lensing effect to be applied to the electron beam A. In the example embodiment shown in FIG. 20, each of the first aperture 2004, the second aperture 2006, and two apertures 2008 are positioned along a midline 2010.

Figure 21:
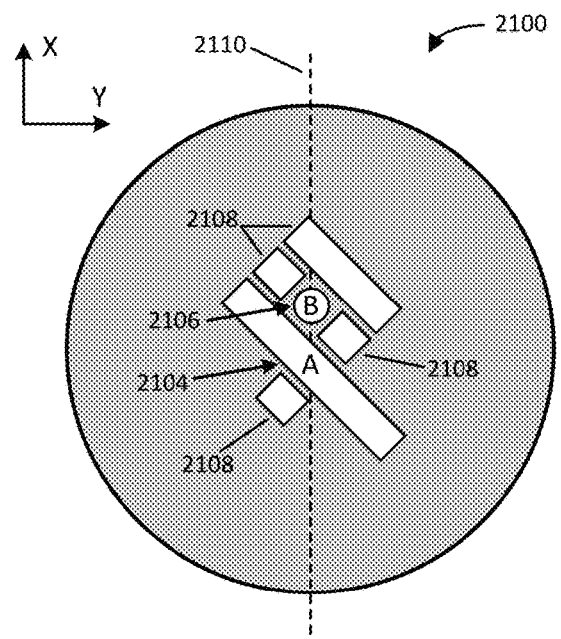

FIGS. 21 and 20 illustrate a pair of component physical structures that can be used to form an aperture defining structure 2306 in the aperture lens array 2500 illustrated in FIG. 25. Specifically, FIG. 21 illustrates an example first component physical structure 2100 of an example aperture defining structure comprising two physical structures. The example first component physical structure 2100 defines (i) a first aperture 2104 that allows a first electron beam to pass through the first component physical structure 2100, (ii) a second aperture 2106 that allows a second electron beam to pass through first component physical structure 2100, and (iii) plurality of other apertures 2108. Such apertures are configured to create a quadrupole lensing effect on electrons passing through the second aperture 2106 during use of the example aperture defining structure. In the example embodiment shown in FIG. 21, each of the first aperture 2104, the second aperture 2106, and other apertures 2108 are positioned along a midline 2110 of the first component physical structure 2100.

Figure 22:
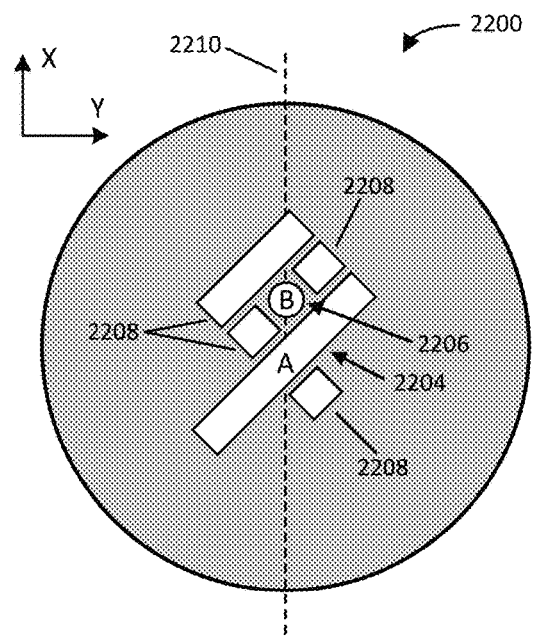

FIG. 22 illustrates an example second component physical structure 2200 of an example aperture defining structure comprising two physical structures. The example second component physical structure 2200 defines (i) a first aperture 2204 that allows a first electron beam to pass through the second component physical structure 2200, (ii) a second aperture 2206 that allows a second electron beam to pass through second component physical structure 2200, and (iii) plurality of other apertures 2208. Apertures 2204 and 2208 are shown as having a geometry similar to the apertures defined by the first component physical structure 2200 illustrated in FIG. 22. The combination of geometry of the second aperture 2106 and the second aperture 2206 causes no net lensing effect to be applied to the electron beam A. Similarly, the geometries of the first aperture 2104 and the first aperture 2204 cause a net quadrupole lensing effect to be applied to the electron beam B as it passes through the second apertures 2106 and 2206. In the example embodiment shown in FIG. 22, each of the first aperture 2204, the second aperture 2206, and two apertures 2028 are positioned along a midline 2210.

FIGS. 23 and 24 illustrate a pair of component physical structures that can be used to form an aperture defining structure 2506 in the aperture lens array 2500 illustrated in FIG. 25. Specifically, FIG. 23 illustrates an example first component physical structure 2300 of an example aperture defining structure comprising two physical structures. The example first component physical structure 2300 defines (i) a first aperture 2304 that allows a first electron beam to pass through the first component physical structure 2300, (ii) a second aperture 2306 that allows a second electron beam to pass through first component physical structure 2300, and (iii) plurality of other apertures 2308. Each of these apertures are illustrated as having a rectangular geometry (e.g., a long slot). Such rectangular apertures are configured to create a cylindrical lensing effect on electrons passing through them during use of the example aperture defining structure. In the example embodiment shown in FIG. 23, each of the first aperture 2304, the second aperture 2306, and two apertures 2308 are positioned along a midline 2310 of the first component physical structure 2300.

FIG. 24 illustrates an example second component physical structure 2400 of an example aperture defining structure comprising two physical structures. The example second component physical structure 2400 defines (i) a first aperture 2404 that allows a first electron beam to pass through the second component physical structure 2400, (ii) a second aperture 2406 that allows a second electron beam to pass through second component physical structure 2400, and (iii) plurality of other apertures 2408. Apertures 2404 and 2408 are shown as having a rectangular similar to the apertures defined by the first component physical structure 2300 illustrated in FIG. 23. This combination of the geometry of the second aperture 2306 and the second aperture 2406 causes no net lensing effect to be applied to the electron beam A. Similarly, the geometries of the first aperture 2304 and the first aperture 2404 cause a net quadrupole lensing effect to be applied to the electron beam B that passes through the second apertures 2306 and 2406. In the example embodiment shown in FIG. 24, each of the first aperture 2404, the second aperture 2406, and two apertures 2408 are positioned along a midline 2410.

FIG. 25 illustrates a cross section of an example aperture lens array 2500 comprising a first electrode 2502, a second electrode 2504, and an aperture defining structure 2506. FIG. 25 shows electrons 2508 being emitted toward a first electrode 2502. The first electrode 2502 is shown as defining a pair of apertures 2512 that allow a portion of the electrons 2508 to pass through the first electrode 2502. In some embodiments, the first electrode 2502 may correspond to an electrically conductive foil that defines the two apertures 2512. A first portion of the electrons 2508 pass through both a first aperture becoming first electron beam 2514. Another portion of the electrons 2508 pass through both the second aperture becoming second electron beam 2516.

In all embodiments, the aperture lens array 2500 includes a second electrode 2504 positioned such that the aperture defining structure 2506 is between the two electrodes. The second electrode 2504 may correspond to a disk electrode defining an aperture 2518 that allows the first electron beam 2514 and the second electron beam 2516 pass through the second electrode 2504.

When certain voltages are applied to both the electrodes 2502 and 2504, and/or aperture defining structure 2506, electromagnetic fields are created between the electrodes 2502 and 2504. The electromagnetic fields and the pattern that the apertures defined by the aperture defining structure 2506 collectively create a lensing effect that causes the first electron beam 2514 and the second electron beam 2516 to have different focal planes.

While non-limiting, a simple representative calculation can be used to illustrate the performance of some embodiments of the present invention having different array patterns for the upstream and downstream components (e.g., the embodiment depicted in FIGS. 19 and 20, the embodiment depicted in FIGS. 21 and 22, the embodiment depicted in FIGS. 23 and 24). To enable this simple representative calculation, the following paragraphs assume that (a) $|\phi_0(z)| \ll U$ everywhere, (b) the field component $E_z = -\phi_0'(z)$ close to the aperture array plates changes from $E_{up}$ (i.e., the nonzero electric field above the aperture defining structure 2506) to 0 in above the aperture defining structure 2306, (c) the field component $E_z = -\phi_0'(z)$ close to the aperture array plates changes from 0 to $E_{low}$ (i.e., the nonzero electric field below the aperture defining structure 2506) below the aperture defining structure 2506, and (d) the field between the array plates is a zero field (e.g. the plates in FIGS. 19 and 20).

In the simple representative calculation, the electrostatic potential up to order 2 in the x and y direction can be generally expressed as:

$$\phi(x,y,z) = U + \phi_0(z) + p\phi_0''(z)x^2 + q\phi_0''(z)y^2 + \phi_2(z)(x^2-y^2), \quad (2)$$

for an electrostatic potential that is mirror symmetric in the x-z plane and the y-z plane. In expression (1), U represents the electron energy above the aperture lens array 2500, and the other terms are induced by the voltages applied to both the electrodes 2502 and 2504, and/or aperture defining structure 2506. The Laplace equation ($\Delta\phi=0$) for this electrostatic potential dictates that $p+q=-1/2$. In some examples, this corresponds to $p=q=-1/4$ for a round aperture lens, and $p=-1/2$ and $q=0$ for a cylinder lens which focuses in the x-z plane (such as the embodiment depicted in FIG. 19).

According to the simple representative calculation, the upstream component of the aperture defining structure 2506 invokes lens strengths:

$$\kappa_{x,up} + f_{x,up}^{-1} = U^{-1}(-p_{up}E_{up} - Q_{up}); \text{ and } \kappa_{y,up} = f_{y,up}^{-1} = U^{-1}(-q_{up}E_{up} + Q_{up}); \quad (3)$$

Similarly, the downstream component of the aperture defining structure 2506 invokes lens strength:

$$\kappa_{x,low} = f_{x,low}^{-1} = U^{-1}(p_{low}E_{low} - Q_{low}); \text{ and } \kappa_{y,low} = f_{y,low}^{-1} = U^{-1}(q_{low}E_{low} + Q_{low}); \quad (4)$$

In these equations, $f_x$ and $f_y$ are the focal distances in the x-z plane and the y-z plane, respectively, and $U^{-1}Q_{up}$ and $U^{-1}Q_{low}$ are the quadrupole lens strengths induced by the quadrupole potential $\phi_2(Z)(x^2-y^2)$.

In some preferred embodiments, $E_{up}=E_{low}=E$. In such embodiments, the total lens strengths simplify to:

$$\kappa_x = \kappa_{x,up} + \kappa_{x,low} = U^{-1}(p_{low}-p_{up})E - Q; \text{ and} \quad (5)$$

$$\kappa_y = \kappa_{y,up}K_{y,low} = U^{-1}(q_{low}-q_{up})E+Q). \quad (6)$$

Because $p_{up}+q_{up}=p_{low}+q_{low}=-1/2$, it follows that $\kappa_y=-\kappa_x$ in such embodiments, meaning that there is only a pure quadrupole lens action.

In embodiments of aperture lens array 2100 where the electromagnetic field is the same on both sides of the physical structures 1900 and 2000, the lensing effects caused by the first electron beam 2108 traveling through the first aperture 1904 are canceled and/or otherwise negated by the lensing effects caused by the first electron beam 2108 traveling through the first aperture 2004. Additionally, in such an embodiment, the lensing effects caused by the second electron beam 2110 traveling through the second aperture 1906 and the lensing effects caused by the second electron beam 2110 traveling through the second aperture 2006 combine to form at least a quadrupole lensing effect.

Figure 26:
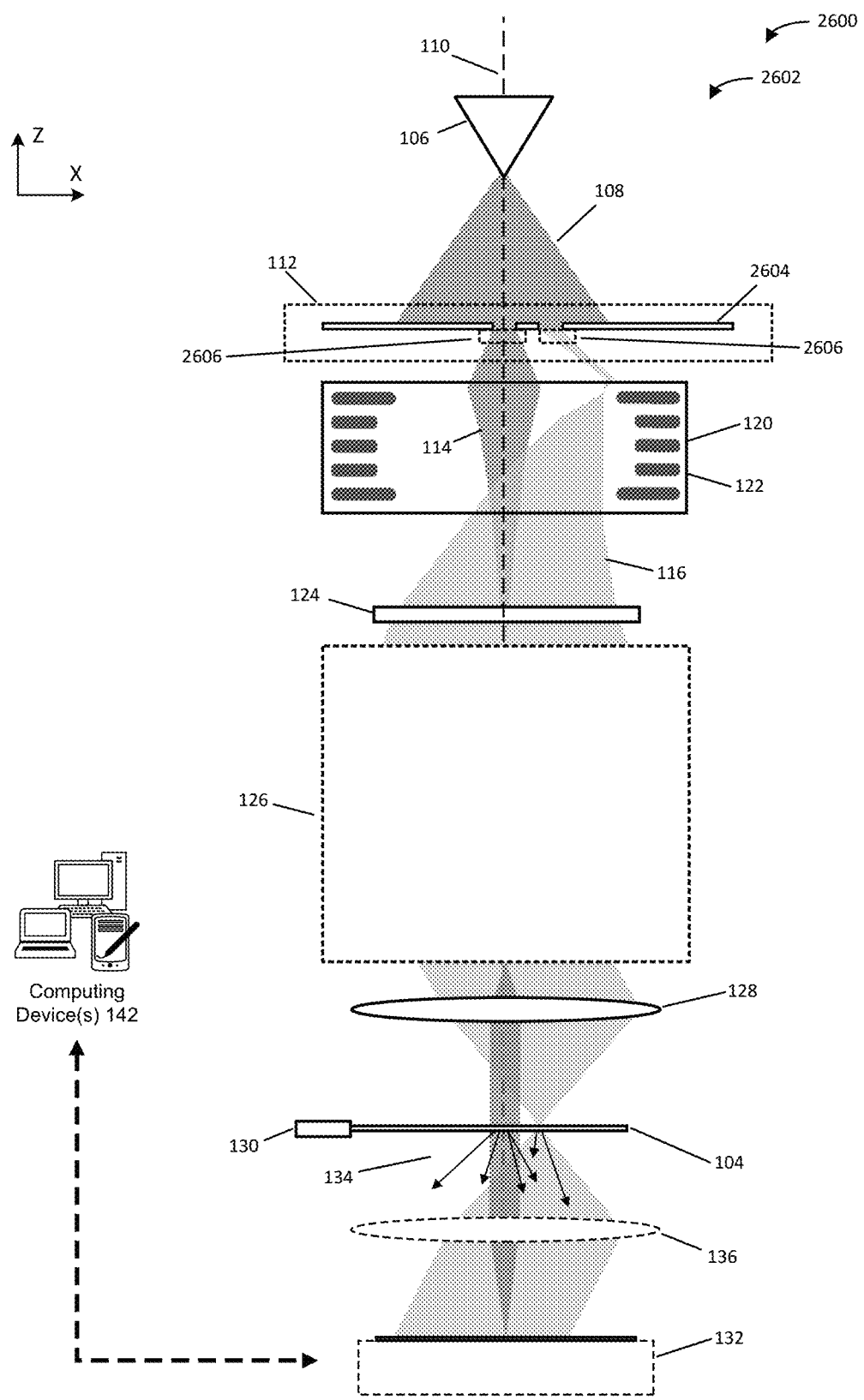
FIG. 26 illustrates example embodiments of bifocal multibeam systems for investigating a sample where the bifocal beamformer comprises a beam splitting mechanism and one or more focusing devices.

FIG. 26 is an illustration of an example embodiment 2600 of bifocal multibeam electron system(s) 100 for investigating a sample 104 where the bifocal beamformer 112 comprises a beamsplitting mechanism 2604 and one or more focusing devices 2606.

The example bifocal multibeam electron system(s) 2602 includes an electron source 106 that emits a plurality of electrons 108 along an emission axis 110 and towards the bifocal beamformer 112. In the illustrated embodiment of the present invention, the bifocal beamformer 112 is shown as comprising at least (i) a beamsplitting mechanism 2604 that splits the plurality of electrons 108 into the first electron beam 114 and the second electron beam 116, and (ii) one or more focusing devices 2606 configured to modify the focal properties of one or both of the electron beams such that the two beams do not have the same corresponding focal planes. In some embodiments, the one or more focusing devices 2606 are further configured to cause one or both of the first electron beam 114 and the second electron beam 116 to be deflected away from the emission axis 110.

In FIG. 26, the beamsplitting mechanism 2604 is shown as corresponding to a physical structure that defines a first aperture that allows the first electron beam 114 to pass through the beamsplitting mechanism 2604, and a second aperture that allows the second electron beam 116 to pass through the beamsplitting mechanism 2604. FIG. 26 further illustrates the one or more focusing devices 2606 as optionally corresponding to two lenses. However, in other embodiments the focusing devices 2606 may correspond to three or more lenses, a single lens that modifies only one of the electron beams, a single lens with a high degree of aberration such that the two electron beams that pass through the lens. Additionally, while FIG. 26 illustrates the beamsplitting mechanism 2604 as being upstream of the one or more focusing devices 2606, in other embodiments of example bifocal multibeam electron systems 2602 the beamsplitting mechanism 2604 may be downstream of the one or more focusing devices 2606. Alternatively, in some embodiment some of the focusing devices 2606 may be upstream of the beamsplitting mechanism 2604, while others of the focusing devices 2606 may be downstream of the beamsplitting mechanism 2604.

FIG. 26 illustrates the bifocal beamformer 112 as being positioned upstream of focusing component 120 that is configured to apply a lensing action that focuses at least one of the first electron beam 114 and the second electron beam 116. In the example bifocal multibeam electron system(s) 2602 shown in FIG. 26, the focusing component corresponds to an accelerator 122 that accelerates/decelerates, focuses, and/or directs the first electron beam 114 and the second electron beam 116 towards a focusing column 126.

The focusing column 126 and the objective lens 128 focus the electron beams 114 and 116 so that they are incident on sample 104. Specifically, FIG. 26 illustrates the focusing column 126 focusing the second electron beam 116 so that it is focused on the sample 104 and the first electron beam 114 such that it is not focused on the sample 104. In some embodiments, the focal properties the first electron beam 114 and the second electron beam 116 are modified such that one of the beams is focused at a plane at or near the sample 104 and the other electron beam is focused at a plane which is located at least 0.1%, 1%, 10%, or 100% of the objective lens focal distance above or below the sample 104. Alternatively or in addition, the focal properties of the first electron beam 114 and the second electron beam 116 may be modified such that the diameter of one of the electron beams at the sample 104 is at least one of 50, 100, 500, or 1000 times greater than the diameter of the other electron beam at the sample.

Examples of inventive subject matter according to the present disclosure are described in the following enumerated paragraphs.

A1. A method for investigating a sample, the method comprising emitting a plurality of charged particles toward the sample; forming the plurality of charged particles into a first charged particle beam and a second charged particle beam; modifying the focal properties of at least one of the first charged particle beam and the second charged particle beam.

A1.1. The method of paragraph A1, wherein modifying the focal properties of at least one of the first charged particle beam and the second charged particle beam comprises modifying one or more of the first charged particle beam and the second charged particle beams such that: the first charged particle beam has a first focal plane; and the second charged particle beam has a second focal plane that is different from the first focal plane.

A1.1.1. The method of paragraph A1.1, wherein modifying the focal properties of at least one of the first charged particle beam and the second charged particle beam comprises modifying one or more of the first charged particle beam and the second charged particle beams such that: the first charged particle beam has a focal plane at a plane at or near the sample; and the second charged particle beam does not have a focal plane at the plane at or near the sample.

A1.1.2. The method of paragraph A1.1, wherein modifying the focal properties of at least one of the first charged particle beam and the second charged particle beam comprises modifying one or more of the first charged particle beam and the second charged particle beams such that: the second charged particle beam has a focal plane at a plane at or near the sample; and the first charged particle beam does not have a focal plane at the plane at or near the sample.

A1.2. The method of any of paragraphs A1-A1.1.2, wherein modifying the focal properties of at least one of the first charged particle beam and the second charged particle beam comprises applying a round lens action to one of the first charged particle beam and the second charged particle beam.

A1.2.1. The method of paragraph A1.2, wherein modifying the focal properties of at least one of the first charged particle beam and the second charged particle beam comprises applying the round lens action to both of the first charged particle beam and the second charged particle beam.

A1.2.1.1. The method of paragraph A1.2.1, wherein the round lens action applied to the first charged particle beam is different from the round lens action applied to the second charged particle beam.

A1.3. The method of any of paragraphs A1-A1.2.1.1, wherein modifying the focal properties of at least one of the first charged particle beam and the second charged particle beam comprises applying at least a quadrupole lens action to one of the first charged particle beam and the second charged particle beam.

A1.4. The method of any of paragraphs A1-A1.3, wherein the first charged particle beam is an axial beam that travels along on an emission axis of the plurality of charged particles, and the second charged particle beam is a non-axial beam.

A1.5. The method of any of paragraphs A1-A1.4, wherein the second charged particle beam is an axial beam that travels along on an emission axis of the plurality of charged particles, and the first charged particle beam is a non-axial beam.

A2. The method of any of paragraphs A1-A1.5, wherein the charged particles are electrons and the charged particle beams are electron beams.

A3. The method of any of paragraphs A1-A2, wherein a second beam diameter of the second charged particle beam at the sample is at least one of 5, 10, 20, 50, 100, 500, or 1000 times greater than a first beam diameter of the first charged particle beam at the sample.

A3.1. The method of paragraph A3, wherein the second beam diameter is at least one of 5, 10, 20, 50, 100, 500, or 1000 times greater than a first beam diameter at or proximate to each crossover point of the first charged particle beam.

A4. The method of any of paragraphs A1-A3.1, wherein the first charged particle beam is tilted with respect to the second charged particle beam at the sample.

A5. The method of any of paragraphs A1-A4, wherein the first charged particle beam and the second charged particle beam are coherent beams.

A6. The method of any of paragraphs A1-A5, further comprising accelerating each of the first charged particle beam and the second charged particle beam to a final energy with an accelerator.

A7. The method of any of paragraphs A1-A5, further comprising accelerating the plurality of charged particles to a final energy with an accelerator.

A8. The method of any of paragraphs A1-A7, wherein each of the forming the plurality of charged particles and the modifying of the focal properties is performed by a bifocal beamformer.

A8.1. The method of paragraph A8 when dependent from A6, wherein the bifocal beamformer is located above an accelerator.

A8.2. The method of paragraph A8 when dependent from A7, wherein the bifocal beamformer is located below an accelerator.

A8.3. The method of any of paragraphs A8-A8.2, wherein the bifocal beamformer distorts the second charged particle beam.

A8.4. The method of any of paragraphs A8-A8.3, wherein the bifocal beamformer changes the focal planes of the second charged particle beam.

A8.5. The method of any of paragraphs A8-A8.4, wherein the bifocal beamformer causes the second charged particle beam to not be a cylindrically symmetric beam.

A8.5.1. The method of paragraph A8.5, further comprising causing the second charged particle beam to be a cylindrically symmetric beam with a stigmator.

A8.6. The method of any of A8-A8.5.1, wherein the bifocal beamformer causes the second charged particle beam to have one or more aberrations.

A8.6.1. The method of paragraphs A8.6, wherein at least one of the one or more aberrations is a deterministic aberration.

A8.6.2. The method of any of paragraphs A8.6-8.6.1, wherein the bifocal beamformer is positioned and/or configured to cause at least one of the one or more aberrations to correct another aberration in the system.

A8.7. The method of any of paragraphs A8-A8.6.2, wherein the bifocal beamformer is further configured to deflect at least one of the first charged particle beam and the second charged particle beam away from an emission axis of the plurality of charged particles.

A9. The method of any of paragraphs A8-A8.7, wherein the bifocal beamformer comprises a MEMS device configured to generate at least a quadrupole lensing effect that at least partially causes the modifying of the focal properties of at least one of the first charged particle beam and the second charged particle beam.

A9.1. The method of paragraph A9, wherein the MEMS device comprises a structure defining a first aperture and a second aperture, and wherein the first charged particle beam passes through the first aperture and the second charged particle beam passes through the second aperture.

A9.1.1. The method of paragraph A9.1, wherein the first aperture has the same radius as the second aperture.

A9.1.2. The method of paragraph A9.1, wherein the first aperture has a smaller radius than the second aperture.

A9.1.3. The method of paragraph A9.1, wherein the first aperture has a greater radius than the second aperture.

A9.1.4. The method of any of paragraphs A9.1-A9.1.3, wherein the MEMS device comprises a surface layer facing the plurality of charged particles, and wherein the first aperture and the second aperture are defined by the surface layer.

A9.1.4.1. The method of paragraph A9.1.4, wherein the surface layer is a foil.

A9.1.5. The method of any of paragraphs A9.1-A9.1.4.1, wherein the first aperture is an axial aperture positioned on an emission axis of the plurality of charged particles, and the second aperture is a non-axial aperture.

A9.1.6. The method of any of paragraphs A9.1-A9.1.4.1, wherein the second aperture is an axial aperture positioned on an emission axis of the plurality of charged particles, and the first aperture is a non-axial aperture.

A9.2. The method of any of paragraphs A9-A9.1.5, wherein the MEMS device comprises one or more electrodes.

A9.2.1. The method of paragraph A9.2, wherein when corresponding voltages are applied to the one or more electrodes, the one or more electrode generates an electromagnetic field that at least partially applies the at least the quadrupole lensing effect.

A9.2.1. The method of any of paragraphs A9.2-A9.2.1, wherein at least one of the one or more electrodes is grounded.

A9.2.2. The method of any of paragraphs A9.2-A9.2.1 when dependent from A9.1.4, wherein the MEMS device comprises an insulating layer that is opposite the surface layer.

A9.2.2.1. The method of paragraph A9.2.2, wherein the one or more electrodes are located in an electrode layer positioned between the insulating layer and the surface layer.

A9.2.3. The method of any of paragraphs A9.2-A9.2.2.1 wherein the one or more electrodes comprise four electrodes.

A9.2.4. The method of any of paragraphs A9.2-A9.2.2.1 wherein the one or more electrodes comprise seven electrodes.

A9.3. The method of any of paragraphs A9-A9.2.4, wherein the at least the quadrupole lensing effect is one of a dipole lensing effect, quadrupole lensing effect, hexapole lensing effect, and octupole lensing effect.

A9.4. The method of any of paragraphs A9-A9.3, wherein the at least the quadrupole field does not cause the focal plane of the first charged particle beam to be changed.

A9.5. The method of any of paragraphs A9-A9.4, wherein the MEMS device is further configured to generate one or more dipole fields.

A9.5.1. The method of paragraph A9.5, wherein the one or more dipole fields cause at least one of the charged particle beams to be deflected in a direction perpendicular to the emission axis.

A9.6. The method of any of paragraphs A9-A9.5.1, wherein the quadrupole lensing effect applies: a positive lens effect to the first charged particle beam in a first meridional plane of the first charged particle beam; and a negative lensing effect to the first charged particle beam in a second meridional plane of the first charged particle beam, wherein the first meridional plane is perpendicular to the second meridional plane.

A9.6.1. The method of paragraph A9.6, wherein a first change of the focal plane of the first charged particle beam in the first meridional plane caused by the quadrupole field is different than a second change of the focal plane of the first charged particle beam in the second meridional plane caused by the quadrupole field.

A9.7. The method of any of paragraphs A9-A9.5.1, wherein the quadrupole lensing effect applies: a positive lens effect to the second charged particle beam in a first meridional plane of the second charged particle beam; and a negative lensing effect to the second charged particle beam in a second meridional plane of the second charged particle beam, wherein the first meridional plane is perpendicular to the second meridional plane.

A9.7.1. The method of paragraph A9.7, wherein a first change of the focal plane of the second charged particle beam in the first meridional plane caused by the quadrupole field is different than a second change of the focal plane of the second charged particle beam in the second meridional plane caused by the quadrupole field.

A10. The method of any of paragraphs A8-A8.6.2, wherein the bifocal beamformer comprises: a physical structure defining a first aperture and a second aperture, wherein the first charged particle beam passes through the first aperture and the second charged particle beam passes through the second aperture; and a lens positioned and/or configured to adjust the focal properties of the at least one of the first charged particle beam and the second charged particle beam such that they have different focal planes.

A10.1. The method of paragraph A10, wherein the first charged particle beam passes through the first aperture and the second charged particle beam passes through the second aperture.

A10.2. The method of any of paragraphs A10-A10.1, wherein the lens is an einzel lens.

A10.3. The method of any of paragraphs A10-A10.2, wherein the lens is positioned above the physical structure.

A10.4. The method of any of paragraphs A10-A10.2, wherein the lens is positioned below above the physical structure.

A10.5. The method of any of paragraphs A10-A10.4, wherein the lens is positioned and/or configured to adjust the focal planes of the second charged particle beam.

A10.5.1. The method of paragraph A10.5, wherein the lens is not positioned and/or configured to adjust the focal planes of the first charged particle beam.

A11. The method of any of paragraphs A6-A6.5, wherein the bifocal beamformer comprises at least one physical structure that defines: a first aperture that allows the first charged particle beam to pass through the at least one physical structure; a second aperture that allows the second charged particle beam to pass through the at least one physical structure; and plurality of other apertures.

A11.1. The method of paragraph A11, wherein the first aperture, the second aperture, and the plurality of other apertures form a pattern that creates an electromagnetic field that applies a lensing effect to the second charged particle beam during use of the bifocal beamformer.

A11.1.1. The method of paragraph A11.1, wherein the first aperture, the second aperture, and the plurality of other apertures form a pattern that creates an electromagnetic field that applies at least a quadrupole lensing effect to the second charged particle beam during use of the bifocal beamformer.

A11.1.1.1. The method of paragraph A11.1.1, wherein the electromagnetic field does not apply the quadrupole lensing effect to the first charged particle beam during use of the bifocal beamformer.

A11.1.2. The method of any of paragraphs A11.1-A11.1.1.1, wherein the first aperture, the second aperture, and the plurality of other apertures form a pattern that creates an electromagnetic field that applies a circular lensing effect to the first charged particle beam during use of the bifocal beamformer.

A11.1.2.1. The method of paragraph A11.1.2, wherein the plurality of other apertures form a pattern that creates an electromagnetic field that applies at least a circular lensing effect to the second charged particle beam during use of the bifocal beamformer.

A11.1.3. The method of any of paragraphs A11.1-A11.2.1, wherein the lensing effect applied by the electromagnetic field at least partially causes the modifying of the focal properties of at least one of the first charged particle beam and the second charged particle beam.

A11.1.3.1. The method of paragraph A11.1.3, wherein the electromagnetic field does change the focal properties of the first charged particle beam.

A11.3. The method of any of paragraphs A11-A11.2.1, wherein at least one aperture of the plurality of apertures is a hole.

A11.3.1. The method of paragraph A11.3, wherein the hole comprises:

an entrance defined in a first surface of the at least one physical structure, the first surface facing the plurality of charged particles; an exit defined in a second surface of the at least one physical structure that is opposite the first surface; and an empty volume that connects the entrance and the exit.

A11.3.1.1. The method of paragraph A11.3.1, wherein the first surface and the second surface are each surfaces of a single physical structure.

A11.3.1.2. The method of paragraph A11.3.1, wherein the first surface and the second surface are each surfaces of a different physical structures.

A11.4. The method of any of paragraphs A11-A11.3.1.2, wherein at least one aperture of the plurality of apertures is a cavity.

A11.4.1. The method of paragraph A11.4, wherein the cavity comprises: an entrance defined in a first surface of the at least one physical structure, the first surface facing the plurality of charged particles; and an empty volume in communication with the entrance and defined by the at least one physical structure, wherein the at least one physical structure defines the empty volume such that a charged particle of the plurality of charged particles that enters the empty volume via the entrance does not pass through the bifocal beamformer.

A11.4.1.1. The method of paragraph A11.4.1, wherein the cavity is defined by a single physical structure.

A11.4.1.2. The method of paragraph A11.4.1, wherein the cavity is defined by multiple physical structures.

A11.5. The method of any of paragraphs A11.3-A11.4.1.2, wherein the plurality of apertures comprises a combination of holes and cavities.

A11.6. The method of any of paragraphs A11-A11.5, wherein the geometry of at least one of the first aperture, the second aperture, or an aperture of the plurality of apertures is circular.

A11.7. The method of any of paragraphs A11-A11.5, wherein the geometry of at least one of the first aperture, the second aperture, or an aperture of the plurality of apertures is rectangular.

A11.7.1. The method of any of paragraphs A11-A11.5, wherein the geometry of at least one of the first aperture, the second aperture, or an aperture of the plurality of apertures is a square.

A11.7.2. The method of any of paragraphs A11-A11.5, wherein the geometry of at least one of the first aperture, the second aperture, or an aperture of the plurality of apertures has rounded corners.

A11.8. The method of any of paragraphs A11-A11.7.2, wherein the geometries of the first aperture, the second aperture, and the plurality of apertures is not uniform.

A11.9. The method of any of paragraphs A11-A11.8, wherein the sizes of the first aperture, the second aperture, and the plurality of apertures is not uniform.

A11.10. The method of any of paragraphs A11-A11.9, wherein the bifocal beamformer further comprises a first electrode configured to receive a first applied voltage.

A11.10.1. The method of paragraph A11.10, wherein the first electrode comprises a physical structure that at least partially defines an electrode entrance aperture that allows at least a portion of the plurality of charged particles to pass through the first electrode.

A11.10.1.1. The method of paragraph A11.10.1, wherein the electrode entrance aperture is a first electrode entrance aperture that allows a first portion of the plurality of charged particles to pass through the first electrode, and the second electrode further defines a second electrode entrance aperture that allows a second portion of the plurality of charged particles to pass through the first electrode.

A11.10.2. The method of any of paragraphs A11.10-A11.10.1.1, wherein the first electrode is upstream of the first aperture, the second aperture, and the plurality of apertures.

A11.10.3. The method of any of paragraphs A11.10-A11.10.2, wherein the first electrode is a disk shaped electrode.

A11.10.4. The method of any of paragraphs A11.10-A11.10.2, wherein the bifocal beamformer further comprises a second electrode configured to receive a second applied voltage.

A11.10.4.1. The method of paragraph A11.10.4, wherein the first voltage is different from the second voltage.

A11.10.4.2. The method of paragraph A11.10.4, wherein the first voltage and the second voltage are different.

A11.10.4.3. The method of any of paragraphs A11.10.4-A11.10.4.2, wherein the second electrode comprises a physical structure that at least partially defines an electrode exit aperture that at least one of the first charged particle beam and the second charged particle beam to pass through the second electrode.

A11.10.4.3.1. The method of paragraph A11.10.4.3, wherein the electrode exit aperture is a first electrode exit aperture that allows the first charged particle beam to pass through the second electrode, and the second electrode further comprises a second electrode exit aperture that allows the second charged particle beam to pass through the second electrode.

A11.10.4.3. The method of any of paragraphs A11.10.4-A11.10.4.3.1, wherein the second electrode is positioned downstream of the first aperture, the second aperture, and the plurality of apertures.

A12. The method of any of paragraphs A8-A8.6.2, wherein the bifocal beamformer comprises a biprism that defines a hole, and which is positioned and/or configured to split the plurality of charged particles into the first charged particle beam and the second charged particle beam.

A13. The method of any of paragraphs A8-A8.6.2, wherein laser pattern fringes are used to split the plurality of charged particles into the first charged particle beam and the second charged particle beam.

A14. The method of any of paragraphs A1-A13, wherein the second charged particle beam is focused at a different plane located above the sample.

A13.1. The method of paragraph A13, wherein the different plane is located at least 0.1%, 1%, 10%, or 100% of the objective lens focal distance above the sample.

A14. The method of any of paragraphs A1-A13, wherein the second charged particle beam is focused at a different plane located below the sample.

A14.1. The method of paragraph A14, wherein the different plane is located at least at least 0.1%, 1%, 10%, or 100% of the objective lens focal distance below the sample.

A15. The method of any of paragraphs A13-A14.1, wherein the distance between the plane at or near the sample and the different plane is at least 0.1%, 1%, 10%, or 100% of the objective lens focal distance.

A16. The method of any of paragraphs A1-A15, wherein the second charged particle beam is a parallel beam at the sample.

A17. The method of any of paragraphs A1-A15, wherein the second charged particle beam is a convergent beam at the sample.

A18. The method of any of paragraphs A1-A15, wherein the second charged particle beam is a divergent beam at the sample.

B1. A method for using electron holography to investigate a sample, the method comprising emitting a plurality of electrons toward the sample; forming the plurality of electrons into a first electron beam and a second electron beam; modifying the focal properties of at least one of the first electron beam and the second electron beam such that the two electron beams have different focal planes; focusing the first electron beam such that it has a focal plane at or near the sample; focusing the second electron beam so that it is incident on the sample, and has a focal plane in the diffraction plane; and detecting an interference pattern of the first electron beam and the diffracted second electron beam in the diffraction plane.

B1.1. The method of paragraph B1, further comprising generating a hologram image of the sample based on the interference pattern of the first electron beam and the diffracted second electron beam in the diffraction plane.

B1.2. The method of any of paragraphs B1-B1.1, further comprising determining the phase of electrons diffracted by the sample based on the interference pattern of the first electron beam and the diffracted second electron beam in the diffraction plane.

B1.3. The method of any of paragraphs B1-B1.2, further comprising determining the exit wave function of the electrons leaving the sample in response to the second electron beam being incident on the sample.

B1.3.1. The method of paragraph B1.3, where determining the exit wave function comprises determining the phase and amplitude of the exit wave function of the electrons leaving the sample in response to the second electron beam being incident on the sample.

B1.3.2. The method of any of paragraphs B1.3-B1.3.1, further comprising determining the structure of the sample based on the exit wave function.

B1.3.2.1. The method of paragraph B1.3.2, wherein the sample is a crystal, and determining the structure of the sample comprises determining the crystal lattice of the sample based on the exit wave function.

B1.4. The method of any of paragraphs B1-B1.3.2.1, wherein the method is repeated at a plurality of sample tilts to obtain a plurality of diffraction holograms, each diffraction hologram of the plurality of diffraction holograms corresponding to a sample tilt of the plurality of sample tilts.

B1.4.1. The method of paragraph B1.4, further comprising determining the crystal structure of the sample based on the plurality of diffraction holograms.

B1.5. The method of any of paragraphs B1-B1.4.1, further comprising determining the phase and amplitude of the diffraction peaks of the interference pattern.

B1.5.1. The method of paragraph B1.5, further comprising determining the crystal structure of the sample based at least in part on the phase and amplitude of the diffraction peaks of the interference pattern.

B1.6. The method of any of paragraphs B1-B1.5.51, further comprising: applying a phase shift to the first electron beam; detecting an additional interference pattern of the phase shifted first electron beam and the diffracted second electron beam in the diffraction plane; and determining a phase of the wave function of a sample exit wave in the diffraction plane based at least in part on the interference pattern and the additional interference pattern, wherein the sample exit wave is resultant from the second electron beam being incident on the sample.

B1.6.1. The method of paragraph B1.6, further comprising further comprising: applying a second phase shift to the first electron beam; detecting a second additional interference pattern of the second phase shifted first electron beam and the diffracted second electron beam in the diffraction plane; and the determination of the phase of the wave function of a sample exit wave in the diffraction plane is based at least in part on the second additional interference pattern.

B2. The method of any of paragraphs B1-B1.5.1, wherein one of the first electron beam and the second electron beam is an axial beam that travels along an emission axis of the plurality of charged particles.

B3. The method of any of paragraphs B1-B2, wherein the diffraction plane corresponds to the first focal plane of the second electron beam downstream of the sample.

B4. The method of any of paragraphs B1-B3, wherein the first electron beam and the second electron beam are coherent.

B4. The method of any of paragraphs B1-B3, wherein the first electron plane passes through an aperture in the sample.

B4.1. The method of paragraph B4, wherein the method further comprises, burning the aperture in the sample with one of an electron beam and an ion beam.

B5. The method of any of paragraphs B1-B3, wherein the first electron beam passes through a thin region of the sample such that there is insufficient scattering to disturb the first electron beam.

B6. The method of any of paragraphs B1-B5, wherein the second electron beam is a parallel beam at the sample.

B6.1. The method of any of paragraphs B1-B5, wherein the second electron beam is a convergent beam at the sample.

B6.2. The method of any of paragraphs B1-B5, wherein the second electron beam is a divergent beam at the sample.

B7. The method of any of paragraphs B1-B6, wherein a second diameter of the second electron beam is greater than 5, 10, 20, 50, and 100 times larger than a first diameter of the first electron beam.

B8. The method of any of paragraphs B1-B7, wherein the first charged particle beam is an axial beam that travels along an emission axis of the plurality of charged particles, and the second charged particle beam is a non-axial beam.

B9. The method of any of paragraphs B1-B7, wherein the second charged particle beam is an axial beam that travels along on an emission axis of the plurality of charged particles, and the first charged particle beam is a non-axial beam.

B10. The method of any of paragraphs B1-B9, wherein modifying the focal properties of at least one of the first electron beam and the second electron beam comprises applying a round lens action to one of the first electron beam and the second electron beam.

B10.1. The method of paragraph B10, wherein modifying the focal properties of at least one of the first electron beam and the second electron beam comprises applying the round lens action to both of the first electron beam and the electron particle beam.

B10.1.1. The method of paragraph B10.1, wherein the round lens action applied to the first electron beam is different from the round lens action applied to the second electron beam.

B11. The method of any of paragraphs B1-B10.1.1, wherein modifying the focal properties of at least one of the first electron beam and the second electron beam comprises applying at least a quadrupole lens action to one of the first electron beam and the second electron beam.

B11.1. The method of paragraph B11, wherein the at least a quadrupole lens action applies an astigmatism to the one of the first electron beam and the second electron beam such that it is no longer a cylindrically symmetric beam.

B11.2. The method of any of paragraphs B11-B11.1, wherein the method further comprises, applying an additional at least a quadrupole lensing effect to the one of the first electron beam and the second electron beam.

B11.2.1. The method of paragraph B11.2, wherein the additional at least a quadrupole lensing effect causes the one of the first electron beam and the second electron beam to be a cylindrically symmetric beam.

B11.2.2. The method of any of paragraphs B11.2-B11.2.1, wherein the at least a quadrupole lensing effect is applied by a corrector.

B11.2.2.1. The method of paragraph B11.2.2, wherein the corrector further applies a deflection perpendicular to an emission axis of the plurality of electrons.

B11.2.2.1.1. The method of paragraph B11.2.2.1, wherein the second electron beam is an axial beam, and the deflection causes the second electron beam to be a non-axial beam downstream of the corrector.

B11.2.2.1.2. The method of paragraph B11.2.2.1, wherein the second electron beam is a non-axial beam, and the deflection causes the second electron beam to be an axial beam downstream of the corrector.

B11.2.2.1.3. The method of paragraph B11.2.2.1, wherein the first electron beam is an axial beam, and the deflection causes the first electron beam to be a non-axial beam downstream of the corrector.

B11.2.2.1.4. The method of paragraph B11.2.2.1, wherein the first electron beam is a non-axial beam, and the deflection causes the first electron beam to be an axial beam downstream of the corrector.

B11.2.2.2. The method of any of paragraphs B11.2.2.1-B11.2.2.1.4, wherein the corrector is positioned at a focal plane of the electron beam that did not receive the at least the quadrupole lensing effect.

B12. The method of any of paragraphs B1-B11.2.2.2, wherein the plurality of electrons are split and the first electron beam and the second electron beam are modified by a MEMS device.

B12.1. The method of paragraph B12, wherein the MEMS device comprises a MEMS device of any of paragraphs F1-F12.1.

B13. The method of any of paragraphs B1-B12, wherein the plurality of electrons are split and the first electron beam and the second electron beam are modified by a multi aperture device.

B13.1. The method of paragraph B13, wherein the MEMS device comprises a MEMS device of any of paragraphs F1-F12.1.

B14. The method of any of paragraphs B1-B13, wherein the sample is a crystal.

B14.1. The method of paragraph B14, wherein the diffraction peaks in the diffraction image are Airy disks.

B15. The method of any of paragraphs B1-B14.1, wherein the electrons scattered by the sample have a focal plane in the diffraction plane.

C1. A system for investigating a sample, the system comprising: a sample holder configured to hold a sample; a charged particle emitter configured to emit charged particles towards the sample; a bifocal beamformer positioned between the charged particle emitter and the sample holder, wherein the bifocal beamformer is configured to: form the plurality of charged particles into a first charged particle beam and a second charged particle beam; and modify the focal properties of at least one of the first charged particle beam and the second charged particle beam such that the first charged particle beam is focused at a plane at or near the sample and the second charged particle beam is not focused at the plane at or near the sample.

C2. The system of paragraph C1, wherein the charged particle emitter is an electron emitter configured to emit electrons toward the sample, and the charged particle beams are electron beams.

C3. The system of any of paragraphs C1-C2, wherein a second beam diameter of the second charged particle beam at the sample is at least one of 5, 10, 20, 50, 100, 500, or 1000 times greater than a first beam diameter of the first charged particle beam at the sample.

C3.1. The system of paragraph C3, wherein the second beam diameter is at least one of 5, 10, 20, 50, 100, 500, or 1000 times greater than a first beam diameter at or proximate to each crossover point of the first charged particle beam.

C4. The system of any of paragraphs C1-C3.1, wherein the first charged particle beam is tilted with respect to the second charged particle beam at the sample.

C5. The system of any of paragraphs C1-C4, wherein the first charged particle beam and the second charged particle beam are coherent beams.

C6. The system of any of paragraphs C1-C5, further comprising an accelerator.

C6.1. The system of paragraph C6, wherein the accelerator is positioned below the bifocal beamformer and configured to accelerate each of the first charged particle beam and the second charged particle beam to a final energy.

C6.2. The system of paragraph C6, wherein the accelerator is positioned above the bifocal beamformer and configured to accelerate the plurality of charged particles to a final energy.

C7. The system of any of paragraphs C1-C6.2, wherein the bifocal beamformer distorts the second charged particle beam.

C8. The system of any of paragraphs C1-C7, wherein the bifocal beamformer changes the focal planes of the second charged particle beam.

C9. The system of any of paragraphs C8-C8.4, wherein the bifocal beamformer causes one of the first charged particle beam and the second charged particle beam to not be a cylindrically symmetric beam.

C9.1. The system of paragraph C9, further comprising a corrector configured to cause the second charged particle beam to be a cylindrically symmetric beam.

C9.1.1. The system of paragraph C9.1., wherein the corrector is a stigmator.

C10. The system of any of C1-C9.1.1, wherein the bifocal beamformer causes the second charged particle beam to have one or more aberrations.

C10.1. The system of paragraphs C10, wherein at least one of the one or more aberrations is a deterministic aberration.

C10.2. The system of any of paragraphs C10-C10.1, wherein the bifocal beamformer is positioned and/or configured to cause at least one of the one or more aberrations to correct another aberration in the system.

C11. The system of any of paragraphs C1-C10.2, wherein the bifocal beamformer is further configured to deflect at least one of the first charged particle beam and the second charged particle beam away from an emission axis of the plurality of charged particles.

C12. The system of any of paragraphs C1-C11, wherein the bifocal beamformer comprises a MEMS device configured to generate at least a quadrupole field that at least partially causes the modifying of the focal properties of at least one of the first charged particle beam and the second charged particle beam.

C12.1. The system of paragraph C12, wherein the MEMS device comprises a structure defining a first aperture and a second aperture, and wherein the first charged particle beam passes through the first aperture and the second charged particle beam passes through the second aperture.

C12.1.1. The system of paragraph C12.1, wherein the first aperture has the same radius as the second aperture.

C12.1.2. The system of paragraph C12.1, wherein the first aperture has a smaller radius than the second aperture.

C12.1.3. The system of paragraph C12.1, wherein the first aperture has a greater radius than the second aperture.

C12.1.4. The system of any of paragraphs C12.1-C12.1.3, wherein the MEMS device comprises a surface layer facing the plurality of charged particles, and wherein the first aperture and the second aperture are defined by the surface layer.

C12.1.4.1. The system of paragraph C12.1.4, wherein the surface layer is a foil.

C12.1.5. The system of any of paragraphs C12.1-C12.1.4.1, wherein the first aperture is an axial aperture positioned on an emission axis of the plurality of charged particles, and the second aperture is a non-axial aperture.

C12.1.6. The system of any of paragraphs C12.1-C12.1.4.1, wherein the second aperture is an axial aperture positioned on an emission axis of the plurality of charged particles, and the first aperture is a non-axial aperture.

C12.2. The system of any of paragraphs C12.1-C12.1.6, wherein the MEMS device comprises one or more electrodes.

C12.2.1. The system of paragraph C12.2, wherein when corresponding voltages are applied to the one or more electrodes, the one or more electrode generate the at least the quadrupole field.

C12.2.1. The system of any of paragraphs C12.2-12.2.1, wherein at least one of the one or more electrodes is grounded.

C12.2.2. The system of any of paragraphs C12.2-C12.2.1 when dependent from C12.1.4, wherein the MEMS device comprises an insulating layer that is opposite the surface layer.

C12.2.2.1. The system of paragraph C12.2.2, wherein the one or more electrodes are located in an electrode layer positioned between the insulating layer and the surface layer.

C12.2.3. The system of any of paragraphs C12.2-C12.2.2.1 wherein the one or more electrodes comprise four electrodes.

C12.2.4. The system of any of paragraphs C12.2-C12.2.2.1 wherein the one or more electrodes comprise seven electrodes.

C12.3. The system of any of paragraphs C12.1-C12.2.4, wherein the at least the quadrupole field is one of a dipole field, quadrupole field, hexapole field, or octupole field.

C12.4. The system of any of paragraphs C12.1-C12.3, wherein the at least the quadrupole field does not cause the focal planes of the first charged particle beam to be changed.

C12.5. The system of any of paragraphs C12.1-C12.4, wherein the MEMS device is further configured to generate one or more dipole fields.

C12.5.1. The system of paragraph C12.5, wherein the one or more dipole fields cause at least one of the charged particle beams to be deflected in a direction perpendicular to the emission axis.

C13. The system of any of paragraphs C1-C11, wherein the bifocal beamformer comprises: a physical structure defining a first aperture and a second aperture, wherein the first charged particle beam passes through the first aperture and the second charged particle beam passes through the second aperture; and a lens positioned and/or configured to adjust the focal properties of the at least one of the first charged particle beam and the second charged particle beam such that they have different focal planes.

C13.1. The system of paragraph C13, wherein the first charged particle beam passes through the first aperture and the second charged particle beam passes through the second aperture.

C13.2. The system of any of paragraphs C13-C13.1, wherein the lens is an einzel lens.

C13.3. The system of any of paragraphs C13-C13.2, wherein the lens is positioned above the physical structure.

C13.4. The system of any of paragraphs C13-C13.2, wherein the lens is positioned below above the physical structure.

C13.5. The system of any of paragraphs C13-C13.4, wherein the lens is positioned and/or configured to adjust the focal properties of the second charged particle beam.

C13.5.1. The system of paragraph C13.5, wherein the lens is not positioned and/or configured to adjust the focal planes of the first charged particle beam.

C14. The system of any of paragraphs C14-C14.5, wherein the bifocal beamformer comprises at least one physical structure that defines: a first aperture that allows the first charged particle beam to pass through the at least one physical structure; a second aperture that allows the second charged particle beam to pass through the at least one physical structure; and plurality of other apertures.

C14.1. The system of paragraph C14, wherein the plurality of other apertures form a pattern that creates an electromagnetic field that applies a lensing effect to the second charged particle beam during use of the bifocal beamformer.

C14.1.1. The system of paragraph C14.1, wherein the plurality of other apertures form a pattern that creates an electromagnetic field that applies at least a quadrupole lensing effect to the second charged particle beam during use of the bifocal beamformer.

C14.1.1.1. The system of paragraph C14.1.1, wherein the electromagnetic field does not apply the quadrupole lensing effect to the first charged particle beam during use of the bifocal beamformer.

C14.1.2. The system of any of paragraphs C14.1-C14.1.1.1, wherein the plurality of other apertures form a pattern that creates an electromagnetic field that applies a circular lensing effect to the first charged particle beam during use of the bifocal beamformer.

C14.1.2.1. The system of paragraph C14.1.2, wherein the plurality of other apertures form a pattern that creates an electromagnetic field that applies at least a circular lensing effect to the second charged particle beam during use of the bifocal beamformer.

C14.1.3. The system of any of paragraphs C14.1-C14.2.1, wherein the lensing effect applied by the electromagnetic field at least partially causes the modifying of the focal properties of at least one of the first charged particle beam and the second charged particle beam.

C14.1.3.1. The system of paragraph C14.1.3, wherein the electromagnetic field does change the focal planes of the first charged particle beam.

C14.3. The system of any of paragraphs C14-C14.2.1, wherein at least one aperture of the plurality of apertures is a hole.

C14.3.1. The system of paragraph C14.3, wherein the hole comprises:

an entrance defined in a first surface of the at least one physical structure, the first surface facing the plurality of charged particles; an exit defined in a second surface of the at least one physical structure that is opposite the first surface; and an empty volume that connects the entrance and the exit.

C14.3.1.1. The system of paragraph C14.3.1, wherein the first surface and the second surface are each surfaces of a single physical structure.

C14.3.1.2. The system of paragraph C14.3.1, wherein the first surface and the second surface are each surfaces of a different physical structures.

C14.4. The system of any of paragraphs C14-C14.3.1.2, wherein at least one aperture of the plurality of apertures is a cavity.

C14.4.1. The system of paragraph C14.4, wherein the cavity comprises:

an entrance defined in a first surface of the at least one physical structure, the first surface facing the plurality of charged particles; and an empty volume in communication with the entrance and defined by the at least one physical structure, wherein the at least one physical structure defines the empty volume such that a charged particle of the plurality of charged particles that enters the empty volume via the entrance does not pass through the bifocal beamformer.

C14.4.1.1. The system of paragraph C14.4.1, wherein the cavity is defined by a single physical structure.

C14.4.1.2. The system of paragraph C14.4.1, wherein the cavity is defined by multiple physical structures.

C14.5. The system of any of paragraphs C14.3-C14.4.1.2, wherein the plurality of apertures comprises a combination of holes and cavities.

C14.6. The system of any of paragraphs C14-C14.5, wherein the geometry of at least one of the first aperture, the second aperture, or an aperture of the plurality of apertures is circular.

C14.7. The system of any of paragraphs C14-C14.5, wherein the geometry of at least one of the first aperture, the second aperture, or an aperture of the plurality of apertures is rectangular.

C14.7.1. The system of any of paragraphs C14-C14.5, wherein the geometry of at least one of the first aperture, the second aperture, or an aperture of the plurality of apertures is a square.

C14.7.2. The system of any of paragraphs C14-C14.5, wherein the geometry of at least one of the first aperture, the second aperture, or an aperture of the plurality of apertures has rounded corners.

C14.8. The system of any of paragraphs C14-C14.7.2, wherein the geometries of the first aperture, the second aperture, and the plurality of apertures is not uniform.

C14.9. The system of any of paragraphs C14-C14.8, wherein the sizes of the first aperture, the second aperture, and the plurality of apertures is not uniform.

C14.10. The system of any of paragraphs C14-C14.9, wherein the bifocal beamformer further comprises a first electrode configured to receive a first applied voltage.

C14.10.1. The system of paragraph C14.10, wherein the first electrode comprises a physical structure that at least partially defines an electrode entrance aperture that allows at least a portion of the plurality of charged particles to pass through the first electrode.

C14.10.1.1. The system of paragraph C14.10.1, wherein the electrode entrance aperture is a first electrode entrance aperture that allows a first portion of the plurality of charged particles to pass through the first electrode, and the second electrode further defines a second electrode entrance aperture that allows a second portion of the plurality of charged particles to pass through the first electrode.

C14.10.2. The system of any of paragraphs C14.10-C14.10.1.1, wherein the first electrode is upstream of the first aperture, the second aperture, and the plurality of apertures.

C14.10.3. The system of any of paragraphs C14.10-C14.10.2, wherein the first electrode is a disk shaped electrode.

C14.10.4. The system of any of paragraphs C14.10-C14.10.2, wherein the bifocal beamformer further comprises a second electrode configured to receive a second applied voltage.

C14.10.4.1. The system of paragraph C14.10.4, wherein the first voltage is different from the second voltage.

C14.10.4.2. The system of paragraph C14.10.4, wherein the first voltage and the second voltage are different.

C14.10.4.3. The system of any of paragraphs C14.10.4-C14.10.4.2, wherein the second electrode comprises a physical structure that at least partially defines an electrode exit aperture that at least one of the first charged particle beam and the second charged particle beam to pass through the second electrode.

C14.10.4.3.1. The system of paragraph C14.10.4.3, wherein the electrode exit aperture is a first electrode exit aperture that allows the first charged particle beam to pass through the second electrode, and the second electrode further comprises a second electrode exit aperture that allows the second charged particle beam to pass through the second electrode.

C14.10.4.3. The system of any of paragraphs C14.10.4-C14.10.4.3.1, wherein the second electrode is positioned downstream of the first aperture, the second aperture, and the plurality of apertures.

C15. The system of any of paragraphs C1-C11, wherein the bifocal beamformer comprises a biprism that defines a hole, and which is positioned and/or configured to split the plurality of charged particles into the first charged particle beam and the second charged particle beam.

C16. The system of any of paragraphs C1-C11, wherein laser pattern fringes are used to split the plurality of charged particles into the first charged particle beam and the second charged particle beam.

C17. The system of any of paragraphs C1-C16, wherein the second charged particle beam is focused at a different plane located above the sample.

C17.1. The system of paragraph C17, wherein the different plane is located at least at least 0.1%, 1%, 10%, or 100% of the objective lens focal distance above the sample.

C18. The system of any of paragraphs C1-C16, wherein the second charged particle beam is focused at a different plane located below the sample.

C18.1. The system of paragraph C18, wherein the different plane is located at least 0.1%, 1%, 10%, or 100% of the objective lens focal distance below the specimen the sample.

C19. The system of any of paragraphs C17-C18.1, wherein the distance between the plane at or near the sample and the different plane is at least 0.1%, 1%, 10%, or 100% of the objective lens focal distance.

C20. The system of any of paragraphs C1-C19, wherein the second charged particle beam is a parallel beam at the sample.

C21. The system of any of paragraphs C1-C19, wherein the second charged particle beam is a convergent beam at the sample.

C22. The system of any of paragraphs C1-C19, wherein the second charged particle beam is a divergent beam at the sample.

D1. Use of the system of any of paragraphs C1-C20 to perform any of the methods of paragraphs A1-A16, B1-B15, L1-L10.2, or M9.1.

E1. A non-transitory computer readable media comprising instructions that, when executed by one or more processing units, cause the system of any of paragraphs C1-C20 to perform any of the methods of paragraphs A1-A16, B1-B15, L1-L10.2, or Ml-M9.1.

F1. A MEMS device, comprising: a physical structure that defines: a first aperture configured to allow a first portion of charged particles of a plurality of charged particles to pass through the MEMS device; and a second aperture configured to allow a second portion of charged particles of the plurality of charged particles to pass through the MEMS device; and one or more electrodes configured to, when corresponding voltages are applied to the one or more electrodes, generate at least a quadrupole field that at least partially causes a modification of the focal properties of at least one of the first portion of charged particles and the second portion of charged particles.

F1.1. The MEMS device of paragraph F1, wherein the plurality of charged particles form a source beam that is incident on the MEMS device.

F1.1.1. The MEMS device of any of paragraphs F1-F1.1, wherein the plurality of charged particles are a plurality of electrons.

F2. The MEMS device of any of paragraphs F1-F1.1.1, wherein the first aperture is configured to form the first portion of charged particles into a first charged particle beam and the second aperture is configured to form the second portion of charged particles into a second charged particle beam.

F2.1. The MEMS device of paragraph F2, wherein the first aperture has the same radius as the second aperture.

F2.2. The MEMS device of paragraph F2, wherein the first aperture has a smaller radius than the second aperture.

F2.3. The MEMS device of paragraph F2, wherein the first aperture has a greater radius than the second aperture.

F3. The MEMS device of any of paragraphs F1-F2.3, wherein the physical structure comprises a surface layer that defines the first aperture and the second aperture.

F3.1. The MEMS device of paragraph F3, wherein the surface layer prevents a third portion of charged particles from passing through the MEMS device.

F3.2. The MEMS device of any of paragraphs F3-F3.1, wherein the surface layer is a foil.

F4. The MEMS device of any of paragraphs F1-F3.2, wherein the first aperture is an axial aperture positioned on an emission axis of the plurality of charged particles, and the second aperture is a non-axial aperture.

F5. The MEMS device of any of paragraphs F1-F3.2, wherein the second aperture is an axial aperture positioned on an emission axis of the plurality of charged particles, and the first aperture is a non-axial aperture.

F6. The MEMS device of any of paragraphs F1-F5, wherein at least one of the one or more electrodes is grounded.

F7. The MEMS device of any of paragraphs F1-F6 when dependent from any of paragraphs F3-F3.1, wherein the MEMS device comprises an insulating layer that is opposite the surface layer.

F7.1. The MEMS device of paragraph F7, wherein the one or more electrodes are located in an electrode layer positioned between the insulating layer and the surface layer.

F8. The MEMS device of any of paragraphs F1-F7.1, wherein the one or more electrodes comprise four electrodes.

F9. The MEMS device of any of paragraphs F1-F7.1, wherein the one or more electrodes comprise seven electrodes.

F10. The MEMS device of any of paragraphs F1-F9, wherein the at least the quadrupole field is one of a dipole field, quadrupole field, hexapole field, or octupole field.

F11. The MEMS device of any of paragraphs F1-F10, wherein the at least the quadrupole field does not cause the focal planes of the first charged particle beam to be changed.

F12. The MEMS device of any of paragraphs F1-F11, wherein the MEMS device is further configured to generate one or more dipole fields.

F12.1. The MEMS device of paragraph F12, wherein the one or more dipole fields cause at least one of the charged particle beams to be deflected in a direction perpendicular to the emission axis.

G1. Use of any of the MEMS devices of any of paragraphs F1-F12.1.

G2. Use of any of the MEMS devices of paragraphs F1-F12.1 to perform any of the methods of paragraphs A1-A16, B1-B15, L1-L10.2, or M1-M9.1.

G3. The use of any of the MEMS devices of paragraphs F1-F12.1 for investigation of a sample.

H1. Use of any of the MEMS devices of paragraphs F1-F12.1 in a system of any of paragraphs C1-C20.

I1. An aperture lens array device comprising: at least one physical structure that defines: a first aperture configured to allow a first portion of charged particles of a plurality of charged particles to pass through the aperture lens array device; a second aperture configured to allow a second portion of charged particles of the plurality of charged particles to pass through the aperture lens array device; plurality of other apertures; and at least one electrode, wherein the first aperture, the second aperture, and the plurality of other apertures form a pattern that, when corresponding voltages are applied to the at least one physical structure and at least one electrode, produces an electromagnetic field that applies a lensing effect to the second portion of charged particles during use of the aperture lens array device.

I1.1. The aperture lens array device of paragraph I1, wherein the plurality of charged particles form a source beam that is incident on the aperture lens array device.

I1.1.1. The aperture lens array device of any of paragraphs I1-I1.1, wherein the plurality of charged particles are a plurality of electrons.

I2. The aperture lens array device of any of paragraphs I.1-I1.1.1, wherein the first aperture is configured to form the first portion of charged particles into a first charged particle beam and the second aperture is configured to form the second portion of charged particles into a second charged particle beam.

I2.1. The aperture lens array device of paragraphs I2, wherein the electromagnetic field applies at least a quadrupole lensing effect to the second charged particle beam during use of the aperture lens array device.

I2.1.1. The aperture lens array device of paragraph I2.1, wherein the electromagnetic field does not apply the quadrupole lensing effect to the first charged particle beam during use of the aperture lens array device.

I2.1.2. The aperture lens array device of any of paragraphs I2-I2.1.1, wherein the electromagnetic field applies a circular lensing effect to the first charged particle beam during use of the aperture lens array device.

I2.1.3. The aperture lens array device of any of paragraphs I2-I2.1.2, wherein the electromagnetic field that at least a circular lensing effect to the second charged particle beam during use of the aperture lens array device.

I3. The aperture lens array device of any of paragraphs I1-I2.1.3, wherein the lensing effect applied by the electromagnetic field at least partially causes a modification of the focal planes of at least one of the first charged particle beam and the second charged particle beam.

I3.1. The aperture lens array device of paragraph I1, wherein the modification of the focal planes caused by the lensing effect causes the first charged particle beam and the second charged particle beam to have different focal planes.

I3.2. The aperture lens array device of any of paragraphs I3-I3.1, wherein the electromagnetic field does change the focal planes of the first charged particle beam.

I4. The aperture lens array device of any of paragraphs I1-I3.2, wherein at least one aperture of the plurality of apertures is a hole.

I4.1. The aperture lens array device of paragraph I4, wherein the hole comprises: an entrance defined in a first surface of the at least one physical structure, the first surface facing the plurality of charged particles; an exit defined in a second surface of the at least one physical structure that is opposite the first surface; and an empty volume that connects the entrance and the exit.

I4.1.1. The aperture lens array device of paragraph I4.1, wherein the first surface and the second surface are each surfaces of a single physical structure.

I4.1.2. The aperture lens array device of paragraph I4.1, wherein the first surface and the second surface are each surfaces of a different physical structures.

I5. The aperture lens array device of any of paragraphs I1-I4.1.2, wherein at least one aperture of the plurality of apertures is a cavity.

I5.1. The aperture lens array device of paragraph I5, wherein the cavity comprises: an entrance defined in a first surface of the at least one physical structure, the first surface facing the plurality of charged particles; and an empty volume in communication with the entrance and defined by the at least one physical structure, wherein the at least one physical structure defines the empty volume such that a charged particle of the plurality of charged particles that enters the empty volume via the entrance does not pass through the bifocal beamformer.

I5.1. The aperture lens array device of paragraph I5.1, wherein the cavity is defined by a single physical structure.

I5.2. The aperture lens array device of paragraph I5.1, wherein the cavity is defined by multiple physical structures.

I6. The aperture lens array device of any of paragraphs I4-I5.2, wherein the plurality of apertures comprises a combination of holes and cavities.

I7. The aperture lens array device of any of paragraphs I1-I6, wherein the geometry of at least one of the first aperture, the second aperture, or an aperture of the plurality of apertures is circular.

I8. The aperture lens array device of any of paragraphs I1-I7, wherein the geometry of at least one of the first aperture, the second aperture, or an aperture of the plurality of apertures is rectangular.

I9. The aperture lens array device of any of paragraphs I1-I8, wherein the geometry of at least one of the first aperture, the second aperture, or an aperture of the plurality of apertures is a square.

I10. The aperture lens array device of any of paragraphs I1-I9, wherein the geometry of at least one of the first aperture, the second aperture, or an aperture of the plurality of apertures has rounded corners.

I11. The aperture lens array device of any of paragraphs I1-I10, wherein the geometries of the first aperture, the second aperture, and the plurality of apertures is not uniform.

I12. The aperture lens array device of any of paragraphs I1-I11, wherein the sizes of the first aperture, the second aperture, and the plurality of apertures is not uniform.

I13. The aperture lens array device of any of paragraphs I1-I12, wherein the at least one electrode comprises a first electrode configured to receive a first applied voltage.

I13.1. The aperture lens array device of paragraph I13, wherein the first electrode comprises a physical structure that at least partially defines an electrode entrance aperture that allows at least a portion of the plurality of charged particles to pass through the first electrode.

I13.1.1. The aperture lens array device of paragraph I13.1, wherein the electrode entrance aperture is a first electrode entrance aperture that allows a first portion of the plurality of charged particles to pass through the first electrode, and the second electrode further defines a second electrode entrance aperture that allows a second portion of the plurality of charged particles to pass through the first electrode.

I13.2. The aperture lens array device of any of paragraphs I13-I13.1.1, wherein the first electrode is upstream of the first aperture, the second aperture, and the plurality of apertures.

I13.3. The aperture lens array device of any of paragraphs I13-113.2, wherein the first electrode is a disk shaped electrode.

I13.4. The aperture lens array device of any of paragraphs I13-113.3, wherein the at least one electrode further comprises a second electrode configured to receive a second applied voltage.

I13.4.1. The aperture lens array device of paragraph I13.4, wherein the first voltage is different from the second voltage.

I13.4.2. The aperture lens array device of paragraph I13.4, wherein the first voltage and the second voltage are the same.

I13.4.3. The aperture lens array device of any of paragraphs I13.4-113.4.2, wherein the second electrode comprises a physical structure that at least partially defines an electrode exit aperture that at least one of the first charged particle beam and the second charged particle beam to pass through the second electrode.

I13.4.3.1. The aperture lens array device of paragraph I13.4.3, wherein the electrode exit aperture is a first electrode exit aperture that allows the first charged particle beam to pass through the second electrode, and the second electrode further comprises a second electrode exit aperture that allows the second charged particle beam to pass through the second electrode.

I13.4.4. The aperture lens array device of any of paragraphs I13.4-113.4.3.1, wherein the second electrode is positioned downstream of the first aperture, the second aperture, and the plurality of apertures.

J1. Use of the multi-aperture device of any of paragraphs I1-I13.4.4.

J2. Use of the multi-aperture device of any of paragraphs I1-I13.4.4 to perform any of the methods of paragraphs A1-A16, B1-B15, L1-L10.2, or M9.1.

J3. The use of the multi-aperture device of any of paragraphs I1-113.4.4 for investigation of a sample.

K1. Use of the multi-aperture device of any of paragraphs I1-113.4.4 in a system of any of paragraphs C1-C20.

L1. A method for investigating a sample with TEM and SEM techniques, the method comprising: emitting a plurality of electrons toward a sample; forming the plurality of electrons particles into a first electron beam and a second electron beam; modifying the focal properties of at least one of the first electron beam and the second electron beam such that: the first electron beam a SEM beam that is focused at a plane at or near the sample; and the second electron beam is a TEM beam that is parallel beam when incident on the sample; detecting emissions resultant from the SEM beam and the TEM beam being incident on the sample.

L2. The method of paragraph L1, further comprising generating one or both of a SEM image and TEM image from the detected emissions resultant from the SEM beam and the TEM beam being incident on the sample.

L3. The method of any of paragraph L1-L2, wherein detecting emissions resultant from the SEM beam and the TEM beam being incident on the sample comprises detecting (1) emissions resultant from the SEM beam being incident and (2) emissions resultant from the TEM beam being incident on the sample, using a same detector and/or detector array.

L4. The method of any of paragraph L1-L3, wherein detecting emissions resultant from the SEM beam and the TEM beam being incident on the sample comprises detecting (1) emissions resultant from the SEM beam being incident and (2) emissions resultant from the TEM beam being incident on the sample, at the same time.

L4.1. The method of paragraph L4, further comprising scanning the SEM beam across a surface region of the sample.

L4.1.1. The method of paragraph L4.1, wherein the TEM beam remains incident on the sample while the SEM beam is scanned.

L4.1.2. The method of any of paragraphs L4.1-L4.1.1, wherein the TEM beam remains incident on a static location while the SEM beam is scanned.

L5. The method of any of paragraph L1-L4.1, further comprising switching between two of a SEM mode of operation, a TEM mode of operation, and a simultaneous SEM/TEM mode of operation.

L5.1. The method of paragraph L5, wherein switching to the SEM mode of operation comprises causing the TEM beam to be blocked so that only the SEM beam is incident on the sample.

L5.1.1. The method of paragraph 5.1, wherein causing the TEM beam to be blocked comprises one of: deflecting the TEM beam so that it is blocked by a beam blocker; moving a beam blocker such that the beam blocker obstructs the path of the TEM beam; and obstructing an aperture so that the TEM beam cannot pass through the aperture.

L5.2. The method of any of paragraph L5-L5.1, wherein switching to the TEM mode of operation comprises causing the SEM beam to be blocked so that only the TEM beam is incident on the sample.

L5.2.1. The method of paragraph 5.2, wherein causing the SEM beam to be blocked comprises one of: deflecting the SEM beam so that it is blocked by a beam blocker; moving a beam blocker such that the beam blocker obstructs the path of the SEM beam; and obstructing an aperture so that the SEM beam cannot pass through the aperture.

L6. The method of any of paragraphs L1-L5.2.1., further comprising determining a portion of the detected emissions that is attributable to the TEM beam being incident on the sample.

L6.1. The method of paragraph L6, further comprising determining a portion of the detected emissions that is attributable to the SEM beam being incident on the sample.

L7. The method of any of paragraphs L1-L6.1, further comprising generating a SEM image based on the detected emissions resultant from the SEM beam and the TEM beam being incident on the sample.

L8. The method of any of paragraphs L1-L7, further comprising generating a TEM image based on the detected emissions resultant from the SEM beam and the TEM beam being incident on the sample.

L9. The method of any of paragraphs L1-L8, wherein the emissions resultant from the SEM beam and the TEM beam being incident on the sample are detected with a single detector and/or detector array.

L10. The method of any of paragraphs L1-L9, wherein the forming of the plurality of electrons particles into a first electron beam and a second electron beam and the modification of the focal properties is performed at least in part by a bifocal beamformer.

L10.1. The method of paragraph L10, wherein the bifocal beamformer is a MEMS device of any of paragraphs F1-F12.1.

L10.2. The method of paragraph L10, wherein the bifocal beamformer is a multi aperture array of any of paragraphs I1-I13.4.4.

L10.2. The method of any of paragraphs L10-L10.2, wherein the bifocal beamformer applies at least a quadrupole lensing effect to one of the first electron beam and the second electron beam.

What is claimed is:

1. A method for using electron holography to investigate a sample, the method comprising
    emitting a plurality of electrons toward the sample;
    forming the plurality of electrons into a first electron beam and a second electron beam;
    modifying the focal properties of at least one of the first electron beam and the second electron beam such that the two electron beams have different focal planes;
    focusing the first electron beam such that it has a focal plane at or near the sample;
    focusing the second electron beam so that it is incident on the sample, and has a focal plane in the diffraction plane;
    detecting an interference pattern of the first electron beam and the diffracted second electron beam in the diffraction plane;
    determining an exit wave function of the exit wave resultant from the second electron beam being incident on the sample; and
    determining the structure of the sample based on the exit wave function.

2. The method of claim 1, wherein the sample is a crystal, and determining the structure of the sample comprises determining the crystal lattice of the sample based on the exit wave function.

3. The method of claim 1, where determining the exit wave function comprises determining the exit wave function of the electrons leaving the sample in response to the second electron beam being incident on the sample, and wherein the structure of the sample is determined based on the exit wave function.

4. The method of claim 3, where determining the exit wave function comprises determining the phase and amplitude of the exit wave function of the electrons leaving the sample in response to the second electron beam being incident on the sample.

5. The method of claim 1, wherein modifying the focal properties of at least one of the first electron beam and the second electron beam comprises applying at least a quadrupole lens action to one of the first electron beam and the second electron beam.

6. The method of claim 1, wherein the diffraction plane corresponds to the first focal plane of the second electron beam downstream of the sample.

7. A method for using electron holography to investigate a sample, the method comprising
    emitting a plurality of electrons toward the sample;
    forming the plurality of electrons into a first electron beam and a second electron beam;
    modifying the focal properties of at least one of the first electron beam and the second electron beam such that the two electron beams have different focal planes;

focusing the first electron beam such that it has a focal plane at or near the sample;

focusing the second electron beam so that it is incident on the sample, and has a focal plane in the diffraction plane; and detecting an interference pattern of the first electron beam and the diffracted second electron beam in the diffraction plane.

8. The method of claim 7, further comprising generating a hologram image of the sample based on the interference pattern of the first electron beam and the diffracted second electron beam in the diffraction plane.

9. The method of claim 7, further comprising determining the relative phases of electrons diffracted by the sample based on the interference pattern of the first electron beam and the diffracted second electron beam in the diffraction plane.

10. The method of claim 7, further comprising determining an exit wave function of the electrons leaving the sample in response to the second electron beam being incident on the sample.

11. The method of claim 10, where determining the exit wave function comprises determining the phase and amplitude of the exit wave function of the electrons leaving the sample in response to the second electron beam being incident on the sample.

12. The method of claim 10, further comprising determining the structure of the sample based on the exit wave function.

13. The method of claim 12, wherein the sample is a crystal, and determining the structure of the sample comprises determining the crystal lattice of the sample based on the exit wave function.

14. The method of claim 7, wherein the diffraction plane corresponds to the first focal plane of the second electron beam downstream of the sample.

15. The method of claim 7, wherein the first electron beam and the second electron beam are coherent.

16. The method of claim 7, wherein the first electron plane passes through an aperture in the sample.

17. The method of claim 16, wherein the method further comprises, burning the aperture in the sample with one of an electron beam and an ion beam.

18. The method of claim 7, further comprising:

applying a phase shift to the first electron beam;

detecting an additional interference pattern of the phase shifted first electron beam and the diffracted second electron beam in the diffraction plane; and determining a phase of the wave function of a sample exit wave in the diffraction plane based at least in part on the interference pattern and the additional interference pattern, wherein the sample exit wave is resultant from the second electron beam being incident on the sample.

19. The method of claim 7, wherein a second diameter of the second electron beam is greater than 20 times larger than a first diameter of the first electron beam.

20. The method of claim 7, wherein modifying the focal properties of at least one of the first electron beam and the second electron beam comprises applying at least a quadrupole lens action to one of the first electron beam and the second electron beam.

* * * * *